United States Patent [19]
Zakim et al.

[11] Patent Number: 5,733,739
[45] Date of Patent: Mar. 31, 1998

[54] SYSTEM AND METHOD FOR DIAGNOSIS OF DISEASE BY INFRARED ANALYSIS OF HUMAN TISSUES AND CELLS

[75] Inventors: David S. Zakim, Armonk; John B. Lord, New York, both of N.Y.

[73] Assignee: InPhoCyte, Inc., White Plains, N.Y.

[21] Appl. No.: 523,972

[22] Filed: Jun. 7, 1995

[51] Int. Cl.⁶ .............. C12Q 1/02; C12Q 1/04; G01N 33/53; G01J 3/28
[52] U.S. Cl. .............. 435/29; 435/40.5; 435/34; 435/40.51; 435/4; 435/366; 435/374; 435/968; 436/171; 436/173; 436/174; 250/338.1; 250/472.1; 250/281; 356/300; 356/326; 128/664
[58] Field of Search .............. 435/29, 40.51, 435/40.5, 34, 968, 4, 366, 373, 374; 436/63, 171, 173, 174; 250/338.1, 472.1, 281; 356/300, 326; 128/664

[56] References Cited

U.S. PATENT DOCUMENTS

| | | | |
|---|---|---|---|
| 3,449,571 | 6/1969 | Hoerman et al. | 436/63 |
| 4,017,192 | 4/1977 | Rosenthal | 436/63 |
| 4,515,165 | 5/1985 | Carroll | 436/63 |
| 4,735,504 | 4/1988 | Tycko | 436/63 |

(List continued on next page.)

FOREIGN PATENT DOCUMENTS

| | | |
|---|---|---|
| 991438 | 6/1976 | Canada. |
| 1019975 | 11/1977 | Canada. |
| 1036385 | 8/1978 | Canada. |
| 1149631 | 7/1983 | Canada. |
| 2008831 | 7/1991 | Canada. |
| 2019865 | 8/1991 | Canada. |
| 2035603 | 8/1992 | Canada. |
| 2050761 | 8/1992 | Canada. |
| 2104960 | 9/1992 | Canada. |
| 1322280 | 9/1993 | Canada. |
| 9215008 | 9/1992 | WIPO. |
| 9303672 | 3/1993 | WIPO. |
| 95/11624 | 5/1995 | WIPO. |
| 9526502 | 10/1995 | WIPO. |

OTHER PUBLICATIONS

Blout, E.R. and Mellors, R.C.; "Infrared Spectra of Tissues"; (1949); Science 110, 137.

Schwarz, H.P., Riggs, H.F., Glick, C., Cameron, W., Beyer, F., Jaffe, B.; Infra Red Spectroscopy of Tissues. Effect of Insulin Shock"; (1951) Proc. Soc. Exptl. Biol. Med. 76, 267.

Wood, D.L.; "Infrared Microspectrum of Living Muscle Cells"; (1951); Science 114, 36.

(List continued on next page.)

Primary Examiner—Louise Leary
Attorney, Agent, or Firm—Hale and Dorr LLP

[57] ABSTRACT

A machine-based method for collecting and interpreting quantitative data on cells and tissues so that a diagnosis will obtain as to the existence or non-existence of disease in an human. Vibrational spectroscopy is used and the spectra generated by such spectroscopy are compared with stored spectra to provide whether cells or tissues are diseased, and if diseased to what degree. It, therefore, is possible to provide a basis for immediate diagnostic decisions for patients and physicians, leading in turn to immediate implementation of next-step procedures and treatment all in one visit to the doctor's office. This means that patients and the examining clinician can know almost instantly whether or not the cells or tissue examined are normal or diseased, and the level of disease present if found. The advantages of bringing the diagnostic pathology service directly into the doctor's office include immediate relief to the patient's concern about health as well as immediate clarification of what needs to be done next in order to treat the disease that is present, and include any other actions that are necessary. The need for biopsies to obtain desired information on the existence or non-existence of disease is obviated. That is, them is a rapid identification of the area of tissue that is affected by disease prior to obtaining biopsies. This makes it possible to apply a single standard of diagnostic accuracy anywhere in the world, independent of the local availability of pathologists or other professionals.

189 Claims, 12 Drawing Sheets

U.S. PATENT DOCUMENTS

| | | | |
|---|---|---|---|
| 4,778,593 | 10/1988 | Yamashita | 356/39 |
| 4,832,483 | 5/1989 | Verma | 356/39 |
| 4,855,243 | 8/1989 | Simic-Glavaski | 436/63 |
| 4,905,169 | 2/1990 | Buican | 356/327 |
| 4,975,581 | 12/1990 | Robinson | 250/339 |
| 5,038,039 | 8/1991 | Wong et al. | 436/63 |
| 5,072,382 | 12/1991 | Kamentsky | 364/413.08 |
| 5,073,498 | 12/1991 | Schwartz | 436/63 |
| 5,107,422 | 4/1992 | Kamentsky | 364/413.08 |
| 5,168,162 | 12/1992 | Oong et al. | 250/339 |
| 5,261,410 | 11/1993 | Alfano et al. | 128/664 |
| 5,281,825 | 1/1994 | Berndt | 250/458.1 |
| 5,408,307 | 4/1995 | Yamamoto | 356/73 |
| 5,596,992 | 1/1997 | Haaland et al. | 128/664 |

OTHER PUBLICATIONS

Morales, J.F., and Cecchini, L.P.; "Some Studies on the Infrared Absorption of the Contractile System of Skeletal Muscle"; J.Cell. Comp. Physiol. 37, 107 (1951).

Schwarz, H.P., Riggs, H.E., Glick, C., McGrath, J., Cameron, W., Beyer, E.; Infra-red Spectroscopy of Brain Tissue. A Lipid Fraction in Normal and Irradiated Adult and Fetal Rats", (1952); Proc. Soc. Exptl. Biol. Med. 80, 467.

Schwarz, H.P., Riggs, H.E., Glick, C., McGrath, J., Childs, R., Bew, E., Stone, F.; Infrared Spectroscopy of Liver Glycogen in Normal and Irradiated Adult and Fetal Rats; (1954); Proc. Soc. Exptl. Biol. Med. 85, 96.

Manfait, M. and Theophanides, T.; "Fourier Transform Infrared Spectra of Cells Treated with the Drug Adriamycin"; (1983); Biochem. Biophys. Res. Communs. 116, 321.

Benedetti, E., Papineschi, F., Vergamini, P., Consolini, R., and Spremolla, G.; "Analytical Infrared Spectral Differences Between Human NOrmal and Leukaemic Cells (CLL)–1"; (1984); Leukemia Research, 8, 483.

Benedetti, E., Palatresi, M.P., Vergamini, P., Papineschi, F., and Spremolla, G.; "New Possibilities of Research in Chronic Lymphatic Leukemia by Means of Fourier Transform–Infrared Spectroscopy—II"; (1985); Leukemia Research 9, 1001.

Freeman, N.K. (1956) Adv. Biol. Med. Phys. 4, 167.

Benedetti, E., Vergamini, P., Spremolla, G.; "FT–IN Analysis of a Single Human Leukemic Cell (Abstract)" Paper presented at the 6th International Conference of Fourier Transform Spectroscopy, Vienna: 87 (1985).

Benedetti, E., Teodori, L., Vergamini, P.; "Fourier Transform Infrared Spectroscopy (FT–IN) with Flow Cytometric Analysis in Tumor Cell Characterization (Abstract)" Basic Appl. Histochem. 31 (Suppl. 2) 14 (1985).

Wong, P.T.T., Zahab, D.M., Narang, S.A., and Sung, W.L.; "High–Pressure Infrared Spectroscopic Study of Human Proinsulin Gene Expression in Live *Escherichia coli* Cells"; Biochem. Biophys. Res. Communs. 146, 232 (1987).

Auger, M., Jarrell, H.C., Smith, I.C.P., Wong, P.T.T., Siminovitch, D.J., and Mantsch, H.H., "Pressure–Induced Exclusion of a Local Anesthetic from Model and Nerve Membranes"; (1987); Biochemistry 26, 8513.

Spremolla, G., Benedetti, E., Vergamini, Andreucci, M.C., Macchia, P.; "An Investigation of Acute Lymphoblastic Leukemia (All) in Children by Means of Infrared Spectroscopy. Part IV"; (1988); Haematologica 73, 21–24.

Parker, F.S. and Ans, R.; "Infrared Studies of Human and Other Tissues by the Attenuated Total Reflection Technique"; (1967); Anal. Biochem. 18, 414–422.

East, E.J., Chang, C.C., Yu, N–T, and Kuck, J.F.R.; "Raman Spectroscopic Measurement of Total Sulfhydryl in Intact Lens as Affected by Aging and Ultraviolet Irradiation"; J. Biol. Chem. 253, 1435–1441 (1985).

Etz, E.S. and Abraham, J.L.; "Molecular Microanalysis of Pathological Specimens in situ with a Laser–Raman Microprobe"; (1979); Science.

Jeannesson, P., Manfait, M., and Jardillier, J.C.; "A Technique for Lawer Raman Spectroscopic Studies of Isolated Cell Populations"; (1983); Anal. Biochem. 129, 305–309.

May, L. and Grenell, R.G.; "Infrared Spectral Studies of Tissues"; Ann. N.Y. Acad. Sci. 69, 171–189 (1985).

Woernley, D.; "Infrared Absorption Curves for Normal and Neoplastic Tissues and Related Biological Substances"; (1952); Can. Res. 12, 561–523.

Wood and Sutherland; Infrared Spectra of Muscle Cells"; (1952); Fed. Proc. 11, 175.

Ozaki, Y., Mizuno, A., and Kaneuchi F.; "Structural Differences between Type I and Type IV Collagen in Biological Tissues Studied in Vivo by Attenuated Total Reflection/ Fourier Transform Infrared Spectroscopy"; Appl. Spect. 46, 626. (1992).

ACCUMULATING DAMAGE TO DNA

WAVENUMBER (1/cm)

SYSTEM AND METHOD FOR DIAGNOSIS OF DISEASE BY INFRARED ANALYSIS OF HUMAN TISSUES AND CELLS

FIELD OF THE INVENTION

The present invention relates generally to systems and methods for diagnosing diseased from non-diseased human tissue and cells. More specifically, the present invention relates to systems and methods for diagnosing diseased from non-diseased human tissue and cells, and for providing for the ability to grade the level of disease in the diseased human tissue and cells that is found.

BACKGROUND OF THE INVENTION

It is known that cancer cells evolve as they accumulate errors in the parts of their DNA that encode factors regulating the growth and division of cells. Cancer emerges when the balance of these factors favors unconstrained growth of cells so that the cells divide without regard for body economy and independent of their location in the body. These properties of cancer cells are tightly regulated in normal cells and dysplastic cells, which have limits on the rates of division and stricter limits on locations in the body in which they can live.

It is also known that there is no single way to describe the sequential, accumulation of errors in cellular DNA that leads ultimately to cancer because there are a multiplicity of factors that regulate the growth of cells. Therefore, an imbalance between factors regulating growth by promoting or constraining it can be arrived at in many different ways.

The evolution of a normal cell to a cancer cell is shown graphically in FIG. 1, generally at 100. In FIG. 1, normal cell 102 may evolve to cancer cell 104 by way of paths 106, 108, 110, 112, or 114. Each path reflects the accumulation of damage to DNA that is different as to the exact sequence or site of damage to DNA and as to the time-dependence for damage to the same sequences of DNA in different patients. The numbers in the boxes in a given path represent specific genes that control growth and change of normal cells. If six genes are mutated, a normal cell will evolve into a cancer cell. As is shown, each path has a different sequence of gene mutation that result in a cancer cell. Although only five paths are shown and six mutations are shown for each path, this is only to be regarded as a representation because there can be a greater number of paths and a greater number of mutations in such paths. Moreover, all paths may not have the same length, if plotted as a function of time, because some damaged sites may lead more rapidly than others to loss or restraint of cell growth and division. Nevertheless, all of the paths lead to a common end-point, which is loss or restraint on cell division and growth and cells with the properties of cancer cells. It, however, is not known whether there is any relation between morphologic grades of dysplasia and the time-dependent progress to cancer according to FIG. 1.

Since specific regions of DNA that are permanently damaged generate abnormal proteins, cell structures leading to the cancerous state will be different even when different patients have cancers of the same type of cell. The impact of this reality has a profound effect on the pathological detection of precancer.

Over the last 30–40 years, there has been numerous efforts to improve upon the ability to obtain early diagnosis of diseased tissue so that effective treatment plans may be devised to arrest or eliminate the disease in the body. This, however, has proven impossible in some cases because at the early stages of a disease, current technology has extreme difficulty detecting the existence of such a disease. Moreover, because of the inaccuracy of current testing methods, there is a large number of false-positives or false-negatives which weigh heavily on the ability to rely on only any single test to determine the existence or non-existence of diseased tissue or cells. This high number of false-positives and false-negatives has had the added effect of eroding patient confidence in his or her physician. Therefore, it is easily understood why patients who have been diagnosed with a disease, such as cancer, do not know who or what to believe about his or her possible illness or whether or not to commence a particular treatment regimen.

The importance of examining cells in the context of controlling the cancer reflects that surgical biopsies cannot be used as a basis for surveillance of millions of people for evidence of the early stages of diseases that lead to cancer because biopsies are difficult, time consuming, and expensive. By contrast, cells can be obtained relatively cheaply via non-invasive or minimally invasive (and safe) methods and, therefore, are ideally suited for purposes of the surveillance of early disease. It is even faster, less costly, and safer to aspirate cells from a tumor through a fine needle than to biopsy the tumor. A problem however, is that diagnostic pathology services are not as accurate in examining cells collected by fine needle aspiration as they are in examining surgical biopsies of the same tumors.

Ironically, the earliest stages of disease are the hardest to detect with current methods of diagnostic pathology. Hence, the pressing need is to improve the results from examining cells. There is a need too for the capacity to follow the evolution of precancerous disease from the earliest time they are detectable in order to determine the most opportune time to intervene therapeutically and to choose for each patient the most efficient and effective form of therapy. Neither of these goals is achieved by current methods of diagnostic pathology.

With respect to PAP smear examinations, it has been recommended that every woman who is sexually active or over the age of 18 have a one of cervical cells once a year. Women take this test to determine the existence or non-existence of cervical cancer.

To perform a PAP smear test, cells obtained by the gentle scraping of the cervix are smeared on glass slides, fixed, stained, and viewed microscopically in order to determine whether the cells are normal or whether they are infected with precancerous disease, which is called "dyplasia." Other diagnoses that are made by examination of the cervical smear are inflammatory response, atypia, and atypical squamous cells of undetermined significance ("ASCUS"). Except for an inflammatory response masking dysplasia or masquerading as dysplasia, the diagnosis of normal cervical cells in the presence of an inflammatory response is not clinically significant. The diagnoses of atypia and ASCUS are extremely troublesome for the clinician because they are equivocal with regard to the absence of dysplasia, which other than "normal" is a key pathologic/cytologic diagnosis.

The validity of diagnostic pathology techniques has been established by the experience of the last 40–50 years in detecting and treating precancerous disease of the cervix. The early detection of precancerous lesions in cervical cells by the technique of examining cervical cells removed by genre scraping of the cervix (the PAP test) has reduced the incidence of invasive cancer of the cervix by about ⅔.

In the United States alone, there are about 50,000 cases of precancer diagnosed per year on the basis of cancer screening via the PAP test. This means that 50,000 American women a year are spared the development of invasive cancer of the cervix because precancerous disease is detected in tissues and cells prior to the evolution of affected cells to cancerous cells. This experience shows, therefore, that it is easier, less costly, and more effective to treat and cure precancerous cells as compared with cancerous cells.

PAP smear tests experience a large percentage of false-negative or false positive results. As such, ⅓ of women with invasive cancer of the cervix have had a recent normal examination of cervical cells, i.e., a normal PAP test. False-negative results, in fact, are as high as 40% for examination of cervical cells. It is clear that screening for precancer of the cervix (and other epithelial tissues as well) needs to be improved.

Once a PAP smear has been completed, the pathologist or cytologist provides a diagnosis of dysplasia. In doing so, he or she indicates the level of the disease seen on smear as CIN I, CIN II, or CIN III based on the extent to which the cells appear abnormal. The relationship of these designations is shown generally in FIG. 2 at 200. As shown in FIG. 2, normal cell 202 will evolve to cancer cell 204 after going through CIN I and 208, CIN II at 212 and CIN III at 214. The CIN I grade at 206 refers to cells that have minimal changes of precancer. The CIN II grade at 208 refer to cells that have moderate changes of precancer. Finally, the CIN III grade refers to cells that are believed to be on the verge of becoming invasive cancers. Such diagnoses alert the clinician that precancer exists and that some type of treatment of the precancer is needed to cure the condition and prevent the ultimate evolution of frank cancer.

In the event that a PAP smear is interpreted as normal, and the clinician has no reason to doubt the accuracy of the diagnosis, nothing further need be done in searching for precancer except to retest the patient in one year. In the event that dysplasia is found or the patient's doctor is suspicious of the meaning of an equivocal diagnosis, e.g., atypia or ASCUS, a culposcopic examination is performed.

Colopscopy is the process of directly viewing the cervix under magnification via an optical device inserted into the vagina. It also involves staining of the tissues with dilute acetic acid to facilitate visualization of abnormalities. The physician biopsies areas of disease during the colposcopic, based on visual evidence of disease and clinical judgment. Sometimes biopsies are taken of the outer region of the cervix even in the absence of identifiable disease. Additionally, biopsies usually are taken of the endocervical tissues that are not accessible by direct visualization during colposcopic. Hence, the PAP smear is used as a screening test for determining whether colposcopy is necessary to confirm the existence of significant disease or to resolve the non-existence of such disease.

Colposcopy and biopsy of cervical tissue regularly detect precancer and cancer in cervical cells in patients in whom PAP smears are normal. In fact, PAP smears detect no more than 50% of women with precancer that have colposcopic examination and subsequent evidence of precancer. The reasons for this include that there is sampling of tissue under direct visualization of diseased areas during colposcopy while not during collection of cells, that biopsies collect tissue at depth while cells may be collected only from the superficial layer of the squamous epithelium of the cervix, and there is greater difficulty in microscopically examining scattered cells versus the examination of contiguous cells in a biopsy. Most importantly, however, biopsies obtained during colposcopy are considered "the gold standard" for determining whether disease is present, and the biopsy of tissue is believed to be the most certain method for detecting or excluding disease.

Typical results of cytologic examinations of cervical cells and histopathologic examinations of cervical biopsies from the same women are summarized in Tables 1 to 3. These results provide graphic examples of the kinds of problems that exist and need to be solved. Table 1, for example, provides data for 15 women that compare the results of cervical cytology (PAP smears) and biopsies of cervical tissue, (obtained at the time of colposcopy).

TABLE 1

| PATIENT # | PAPRESULT | BIOPSY RESULT |
|---|---|---|
| PATIENT 1 | LOW GRADE CIN | CINII-III |
| PATIENT 2 | ASCUS | CINI |
| PATIENT 3 | LOW GRADE CIN | CINI |
| PATIENT 4 | ASCUS | CINI |
| PATIENT 5 | NEGATIVE | CINII |
| PATIENT 6 | LOW GRADE CIN | CINII |
| PATIENT 7 | ASCUS | CINI |
| PATIENT 8 | LOW GRADE CIN | CINI |
| PATIENT 9 | LOW GRADE CIN | CINII |
| PATIENT 10 | HIGH GRADE CIN | CINII-III |
| PATIENT 11 | HIGH GRADE CIN | CINI |
| PATIENT 12 | HIGH GRADE CIN | CINII |
| PATIENT 13 | LOW GRADE CIN | CINIII |
| PATIENT 14 | NEGATIVE | CINI |
| PATIENT 15 | SQ. ATYPIA CAN'T R/O CIN1 | CINIII |

As is seen, there is poor correspondence between the diagnoses made by examination of cervical cells and the diagnosis made on the basis of cervical biopsies.

The problem of making accurate diagnoses is illustrated further by the results in Table 2, which shows the results of diagnosis made by four pathologists on the same data of 16 patients.

TABLE 2

| PATIENT | ORIGINAL SIGNED OUT | PATH 1 | PATH 2 | PATH 3 | PATH 4 |
|---|---|---|---|---|---|
| PATIENT 1 | LG-SIL REC COLPO | 1 ASCUS | 2 LG | 1 HG | |
| PATIENT 2 | ATYPIA UNDET. SIGN. | 1 REACT | 1 ASCUS | 1 LG | 1 HG |
| PATIENT 3 | LG-HPV REC COLPO | 1 ASCUS | 3 LG | | |
| PATIENT 4 | ASCUS/COLPO | 1 SQMET | 2 INF | 1 ASCUS | |
| PATIENT 5 | NEG FOR MC | 1 ASCUS | 1 INF | 1LG | 1HG |
| PATIENT 6 | LG/HPV REC COLPO | 2 ASCUS | 2 LG | | |
| PATIENT 7 | ASCUS | 3 LG | 1 HG | | |
| PATIENT 8 | LG-SIL | 2 ASCUS | 1 LG | 1 HG | |
| PATIENT 9 | LG/HPV | 2 LG | 2 LG/HG | | |
| PATIENT 10 | NO PAP ON FILE | | | | |

TABLE 2-continued

| PATIENT | ORIGINAL SIGNED OUT | PATH 1 | PATH 2 | PATH 3 | PATH 4 |
|---|---|---|---|---|---|
| PATIENT 11 | HG | 2 INF | 1 LG | 1HG | |
| PATIENT 12 | HG-SIL ADVISE COLPO | 1 INF/LG | 1 LG | 2 HG | |
| PATIENT 13 | HG, MOD DYS | 2 LG | 2 HG | | |
| PATIENT 14 | LG-SIL ADVISE COLPO | 1 ASC/LG | 1 LG | 2 HG | |
| PATIENT 15 | NEG INFLAM CELL CHANGES | 1 ASCUS | 2 LG | 1 HG | |
| PATIENT 16 | SQ ATYPIA/CAN'T R/O LG | 1 ASCUS | 1 LG | 2 HG | |

LG = Low Grade
INF LAM = Inflammation
COLPO = Colopscopy
HPV = Human papilloma virus
HG = High Grade
SQMET = Squamous Metaplasia
REC = Recommend
SIL = Squamous Intraepithelial Lesion
NEG = Negative
ASCUS = Atypical Squamous Cells Undetermined Significance As stated, listed are the individual diagnoses of four pathologists, who examined the same smears of cervical cells without knowledge of diagnoses reached by other pathologists. Table 2 shows poor agreement between pathologists examining the same cells. As will be seen in Table 3, the inter-individual variation in diagnosis does not improve when cervical biopsies are examined.

Table 3 shows the individual diagnoses of four pathologists examining independently the biopsies corresponding to the cervical cells.

TABLE 3

| PATIENT | ORIGINAL SIGNOUT | PATH 1 | PATH 2 | PATH 3 | PATH 4 |
|---|---|---|---|---|---|
| PATIENT 1 | CINII-III | 1 CINII/III | 1 CIN/HPV | 2 CINS/CIS | |
| PATIENT 2 | CINI/HPV | 1 INF ATY | 2 CIN I | 1 CINI/HPV | |
| PATIENT 3 | CINI | 1 HPV | 1 CINI/HPV | 2 CINI | |
| PATIENT 4 | CINI | 3 CINI | 1 CINIII | | |
| PATIENT 5 | CINII | 1 CINI/II | 2 CINII/III | 1 CINIII | |
| PATIENT 6 | CINII | 1 CINI/II | 1 CINI/HPV | 1 CINII | 1 CINIII |
| PATIENT 7 | CINI/HPV | 1 CINI | 1 CINI-II | 1 CINII/HPV | 1 CINII/III |
| PATIENT 8 | CINI/HPV | 1 INF CH | 1 HPV | 1 CINI/HPV | 1 CINIII/CIS |
| PATIENT 9 | CINII/HPV | 2 CINI | 2 CINI/HPV | | |
| PATIENT 10 | CINI-II | 1 CINI/HPV | 1 CINI/II | 1 CINII/HPV | 1 CINII/III |
| PATIENT 11 | CINII-III | 1 CINI | 2 CINI/II | 1 CINII/HPV | |
| PATIENT 12 | CINI | | 1 CINI/II | 3 CINII | |
| PATIENT 13 | CINII | 2 CINI/II | 2 CINII | | |
| PATIENT 14 | CINIII | 2 CINIII | 2 CINIII/CIS | | |
| PATIENT 15 | CINI-II | 1 CINII | 3 CINII/III | | |
| PATIENT 16 | CINIII | 1 CINII/III | 1 CINIII | 1 CIS | |

Table 3 demonstrates the generally poor agreement between pathologists as to the exact diagnoses when made by examining the same cervical biopsies. In fact, there is a significant discrepancy between pathologists as to the type of disease present, given that dysplasia (CIN) is a serious problem while diagnoses such as inflammatory response, reactive response, or squamous metaplasia are not medically significant. Moreover, there is virtually no agreement on grading the degree of dysplasia.

As stated the pathologists' view of the evolution of normal cells to cancer as depicted in FIG. 2. The cells evolve along a linear and singular path from normal to frank cancer. This idea has considerable clinical value because it suggests that the extent and rate of progression of precancer can be tracked in patients, that the examination of cells and tissues allows for predicting the rate of approach to cancer, that the selection of the most optimum time and type of therapy for each patient can be chosen, and that the efficacy of agents that are purported to affect the rate of progression of cells to cancer can be determined. In practice, however, the classification in FIG. 2 and the idea expressed by it are of no value clinically because the designations of CIN I to III are essentially arbitrary and the realities of what is shown in FIG. 1 must be considered.

No attempt has been made to use what is shown in FIG. 2 for the purpose of tracking the course of disease in individual patients. A woman's past PAP smears or cervical biopsies are almost never compared with current ones for the purpose of tracking the course of her disease. The grading system is used only for selecting treatment at a single point in time; but even when used this way, the examples in Table 3 indicate that the grading system is unlikely to optimize the selection of therapy. Thus, women may be treated for cervical disease not so much according to their real disease but according to the pathologist's subjective interpretation of the tissue or cells obtained for examination.

The diagnostic pathology services that are used to perform the work discussed above have inherent limitations. These limitations restrict the usefulness of the diagnostic activity and impact negatively on the practice of clinical medicine. One of the main reasons for this is that diagnostic pathology services are completely subjective.

Under current methods, the collection of information from tissue or cells may result in interpretations of such information that varies tremendously because these interpretations are subjective and not based on some standard. For example, current diagnosis of disease may be obtained by microscopic examination of fixed, stained tissues. During examination, the examiner looks for clues that indicate whether a particular disease is present. A few of the things that the examiner will look for in this evaluation are changes in the size and shape of components in cells, the amounts of different components (for example, the volume occupied by the nucleus of the cell as compared with the total volume of the cell), and the intensity with which components stain. The evaluation of these items will depend solely on the examining pathologist, his background, and his experience.

The type of evolution just described did not at any stage attempt to assign numerical value to or weight to various diagnostic criteria or to quantatate how abnormal cells differ from normal. Judgments were made only on the existence or non-existence of diseased tissue and cells. What complicates the evaluation process further is that not all cells in a section of tissue or on a slide are affected equally, if affected at all. Also, the examiner often is looking for a few diseased cells amongst a large number of normal appearing cells which is like trying to find a "needle in a haystack," which is not usually fruitful.

Because of the subjective nature of data collection by an examiner and subjective interpretation of the medical relevance of the data, there is a crucial relationship between the validity of a diagnostic opinion and the skill, diligence, and prior experience of the examiner; and the presence of factors that affect skill; e.g., fatigue and time-demands in the work place. The results of these factors are that the quality of diagnostic services can vary widely in different locations. There are no ways to control these variations so long as the fundamental method of diagnostic pathology remains a subjective process.

Even when levels of skill and experience in collecting information are considered equal and fatigue is not a complicating factor, the subjective nature of the diagnostic process is reflected by high rates of disagreement between different pathologists as to what each saw in a sample of tissue or cells as has been discussed. The variability, even applies when a single pathologist views the same sample at different points in time which results in that examiner often disagreeing with his or her prior diagnosis.

The issue of subjectivity also results in the diagnostic pathology services being provided only by pathologists. As such, such services will not be available in the absence of trained pathologists in reasonable proximity to sites at which samples of tissues and cells are collected. Moreover, diagnostic pathology services are not available in many parts of the world because of the lack of trained personnel. Therefore, when such services are performed without the assistance of trained pathologists, the quality of these services is extremely poor.

Another issue is that the current knowledge of the causes and evolution of diseases, such as cancer, exceed the diagnostic capabilities of current pathology to reliably detect evidence of the early stages of a disease or its forerunner. As such, there is a failure to bring the maximum clinical benefit to patients that have, for example, a precancerous disease that can be treated if attacked early enough. More particularly with respect to cancer, the current knowledge of the causes and evolution of cancer exceed the diagnostic powers of pathology to reliably detect evidence of the emergence of cancer from precancerous cells. Therefore, it is only after the diseased tissue or cells reach a threshold level that any detection can be made, which may be too late.

What is not always appreciated is that normal cells do not become cancerous suddenly or in one step but develop over a period of time in a series of steps. If, in fact, one is able to have a detection system and method that can detect precancer at the earliest stages through frank cancer, it would be extremely helpful in the fight against cancer and other diseases.

A further problem with diagnostic pathology services is that they are not suitable for monitoring, in real-time, the effect of a treatment regimen on the evolution of the disease, such as cancer, from early stages, such as precancerous cells. Physicians need a real-time method for evaluating whether the progression of precancerous disease is responding to treatment. Real-time analysis of progress of disease in a given patient is especially important so a physician can accurately determine whether chemoprotective agents, which are used for the purpose of slowing the evolution of cancer from normal or even precancerous tissues, actual work.

By real-time, what is meant is that a system would have the capacity to determine the rate of progression of disease in each individual patient by comparing the properties of cells taken at different times from the patient. This may seem to be a simple, but it is not possible to do it with current methods of diagnostic pathology. Current methods cannot grade accurately the extent of progress of precancerous disease in an individual patient. The course of disease and the response of disease to therapy are only accessible today via retrospective epidemiologic studies that give, at best, the average course of a disease and the average response of that disease to treatment.

Also diagnostic pathology services are dependant on the adequacy of samples submitted for analysis. In order for diagnostic pathology services to obtain a diagnosis, they must have an adequate amount of tissue or cells. Therefore, in the absence of the proper quantity, a diagnosis cannot be provided. Without quality control standards to ensure that an adequate amount of cells is provided, there is an inherent diminution in the value of the diagnostic procedure.

In some applications of the current methods of pathology, and especially in the examination of individual cells, the value of examination depends on the quality of the specimen collected as well as the subjective collection of information from the sample. Variation in the number of cells available for examination in samples of cervical cells can be as great, from patient to patient, as 1000-fold. Yet this disparity almost never becomes an issue because of what is done in reality.

Reports of inadequate samples are embarrassing to the referring physician, who must recall the patient and explain the need for acquiring a new sample. There is a tendency, therefore, for laboratories to protect their business interests by protecting referring physicians from the embarrassment of having collected an inadequate sample.

Another control issue is that laboratories, responding to economic issues, do not follow recommended guidelines for sampling and examining cervical cells. The recommended method for obtaining cells and examining them is to obtain separately cells from the endo- and exocervix, and to smear cells from the two locations on separate slides. This recommended method for sampling cervical cells generally is ignored because it doubles the cost of performing the diagnostic examination. The same fee can be collected, however, by examining a single slide that presumably has a mixture of cells from the endo- and exocervical regions as for the recommended two-slide method (which takes more time). Therefore, in many cases, the single slide method is used.

Other issues to consider are the economics of diagnostic pathology services and the time involved to perform the services. The separation of the tissue and cells from the patient, and transportation to a location of the specialized technicians and then to the pathologist or cytotechnologist, lead to long delays between acquiring samples and rendering diagnostic opinions. Moreover, this adds considerably to the total cost of medical care. In some instances too, in which speed is essential for the diagnostic process, as for example in the operating room, the methods used to speed the diagnostic process from days to hours or to minutes are inherently inferior to more time-consuming methods.

These and other problems are addressed by the system and method of the present invention.

SUMMARY OF THE INVENTION

The present invention is a machine-based method for collecting and interpreting quantitative data on cells and tissues. The present invention makes it possible to provide high quality diagnostic pathology services in medically-underserved regions of the world, including the United States. The present invention provides a basis for immediate diagnostic decisions for patients and physicians, leading in turn to immediate implementation of next-step procedures and treatment all in one visit to the doctor's office. This means that patients and the examining clinician can know almost instantly whether or not the cells or tissue examined are normal or diseased, and the level of disease present if found. The advantages of bringing the diagnostic pathology service directly into the doctor's office include immediate relief to the patient's concern about health as well as immediate clarification of what needs to be done next in order to treat the disease that is present, and include any other actions that are necessary.

In the case that a sample is judged inadequate for making a reasonably certain diagnosis, a new sample can be obtained before the patient leaves the doctor's office. This adds to the quality of diagnostic services without inconveniencing the patient or doctor and adds little cost to the process of making the most accurate diagnosis possible.

The present invention also solves another critical but often neglected feature of the cost of delivering medical care, which is the cost of patients with disease who are lost to proper follow-up treatment while disease is present in early and curable stages. Patients at the highest risk for cancer of the cervix, for example, are the ones most often lost to follow-up (as often as 25% of the time) after a positive PAP smear test. A major contributing factor to this loss to follow-up is the long delay between collecting cervical cells from the patient and the rendering of a diagnosis. Because of the delay between collecting a specimen of cells and the final diagnostic opinion of the pathologist, the impact of the diagnostic decision is diminished. It is often not delivered in person by the patient's doctor in the immediate clinical setting. The important problem of loss to follow-up of patients with treatable diseases will be decreased in the setting that patients and doctors know the diagnosis at the time cervical samples (or other samples) are collected. The present invention also makes it possible for the clinician to have an immediate comparison of results of previous tests with the test being conducted at the moment, whether or not the previous and the present tests were conducted by the same physician at the same location.

There are medically compelling reasons why diagnosis should be carried out prior to or without obtaining biopsies of tissues or cells. The present invention makes this possible because by using a probe it collects exactly the same type of information about cells and tissues within the body as it collects from examining cells and tissues removed from the patient by biopsy. The medical importance of this aspect of the present invention is not simply to allow for gathering immediate diagnostic information from the patient but is to provide the ability to obtain more information from broader areas by examining tissues inside the body than is available by taking biopsies or cells from the body and then examining them. For example, the act per se of biopsy of tissue distorts the remaining tissue and bleeding that accompanies a biopsy distorts the physicians visual field of the diseased tissue. These limit the number of biopsies that can be obtained. Not infrequently, biopsies of suspicious tissues are reported as "normal," which leads to recalling the patient, repeating the procedure, and obtaining even more biopsies. Additionally, biopsies cannot be taken in patients who have been placed on anticoagulants or who have taken aspirin and related drugs within a few days of the examination.

The present invention provides a means for rapid identification of the area of tissue that is affected by cancer or another disease prior to obtaining biopsies at the presumed margins between normal and diseased tissues. This information, in turn, allows the surgeon to make immediate and accurate decisions as to what portions of tissue to leave behind or remove. Moreover, the present invention provides a rapid, objective measure of the state of the tissue, which can be used to follow the patient's course after surgery.

Noting the foregoing, an object of the present invention is to provide a non-subjective, quantitative system and method for the collection of data from cells and tissues and to make interpretations about the presence or absence of disease based on evaluation of these data. This objective makes it possible to apply a single standard of diagnostic accuracy anywhere in the world, independent of the local availability of pathologists or other professionals.

A further object of the present invention is to provide quantifiable diagnostic tools for determining when to treat patients with precancer, how to treat these patients, and whether or not these patients are responding to non-surgical therapies.

Another object of the present invention is to solve the problem of quality control of sampling by providing an objective, and quantifiable measure of the adequacy of samples of cells submitted for examination by providing doctors and patients with results based on the adequacy of the samples submitted for examination.

A still further object of the present invention is to ensure that as much clinically useful information is derived by examining cells which is accomplished because the marginal, incremental cost of examining multiple cytological samples from a single patient, makes it possible to collect and examine cells in the field.

Another object of the present invention, in the context of examining tissue within the body, is to provide a means for rapid identification of diseased tissues in the setting of the operating room.

These and other objects of the invention will be described in the remainder of the specification referring to the drawings.

DESCRIPTION OF THE INVENTION

Figure 1:
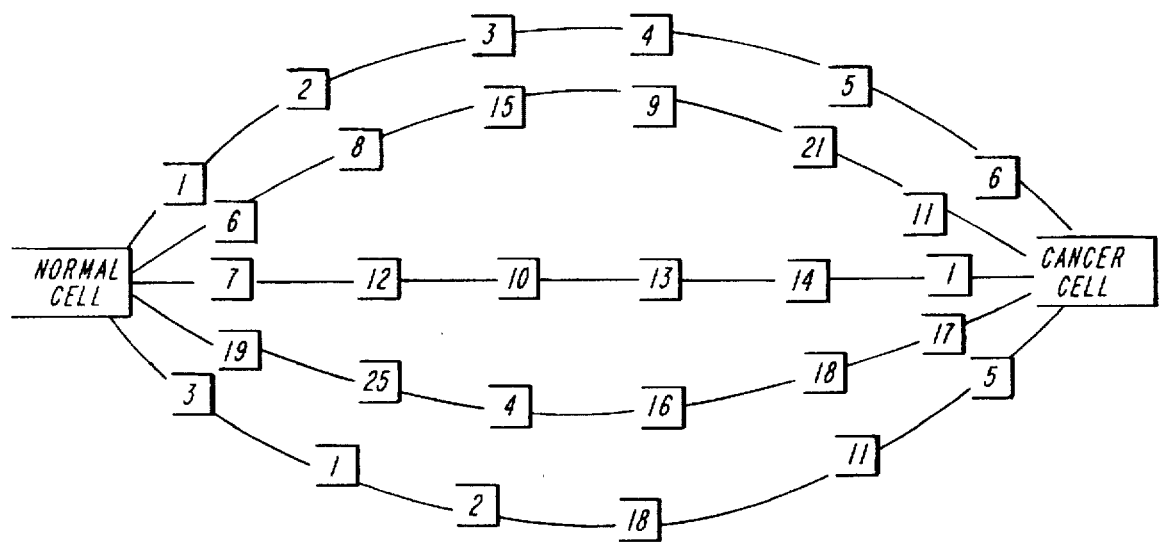
FIG. 1 graphically shows live possible multipaths for cells evolving from normal to cancerous.

The present invention is a machine-based system and method for determining whether tissues or cells are diseased and grading the level of diseased cells. According to the present invention, vibrational spectroscopy is used to detect disease in cells at a significantly high level of discrimination. This discrimination level is much higher than is able to be obtained using any of the various microscopic methods. The present invention may be associated with the vibrational spectroscopy data collection systems and methods described in co-pending application Ser. No. 08/485366, titled Biological Cell Sample Holding for Use in Infrared and/or Raman Spectroscopy Analysis, and filed Jun. 7, 1995.

Data Collection and Detection.

In the context of spectroscopy, vibrational spectra of molecules, e.g., the absorption of light in the infrared spectrum light energies or Raman scattering of light at various frequencies, provide a method for examining the chemical and physical structures of molecules including the complex molecules in living cells, such as lipids, complex sugars, proteins, and nucleic acids which account for the biological behavior and characteristics of cells. Vibrational spectroscopy can be used on complex systems, such as intact cells and tissues, and the spectra that is generated provide useful information about the normalcy of the cells and tissues examined so that a reasonable standard may be determined. Vibrational spectroscopy applied to intact cells may be used to distinguish between normal cells and cells with the pathological features of disease such as cancer. For example, infrared spectra may be used to distinguish benign breast tumor cells from normal cells and infrared spectroscopy may be used to detect aberrant proteins in cell. Raman spectroscopy may be used to detect the accumulation of lipid in atherosclerotic disease of blood vessels. The depletion of glycogen in response to hormonal imbalance may be detected by infrared spectroscopy, as may be differences in an organ of origin of normal tissues. Additionally, the presence of foreign molecules in cells and the effects of these molecules on selected regions of cells may be detected with infrared spectroscopy. The damaging effects of ionizing radiation, different functional states of muscle, and age and light-induced damage to the eye also may be detected with various modes of vibrational spectroscopy.

There has been some work in the past with regard to the use of infrared spectroscopy to detect cancer of the cervix just as it has been used to detect different cancers in other tissues examined to date via infrared spectroscopy. Infrared spectroscopy also has been found to be useful in detecting cancer in other epithelial cells, such as skin, lung, breast, and colon. U.S. Pat. Nos. 5,038,039 filed Aug. 6, 1991 and 5,168,162 filed Dec. 1, 1992 to Wong et al. show the use of infrared spectroscopy to detect changes in cervical cells that are dysplastic. These patents, however, do not address or recognize that the different stages of dysplasia can be discriminated from each other by infrared examination of cervical cells and/or tissues.

As illustrated in Tables 1 to 3, there has been considerable work directed to obtaining information based with the microscopic examination of tissue. There has not been, however, any teaching or consideration for obtaining the same type of information in a way that allows for standardization even taking into account the various modalities of vibrational spectroscopy. The present invention uniquely uses infrared spectroscopy and also other modes of vibrational spectroscopy to provide a level of information about disease that is not accessible by other known methods and a level of information about disease that goes beyond what can be provided by current pathological interpretations of tissue.

Figure 3:
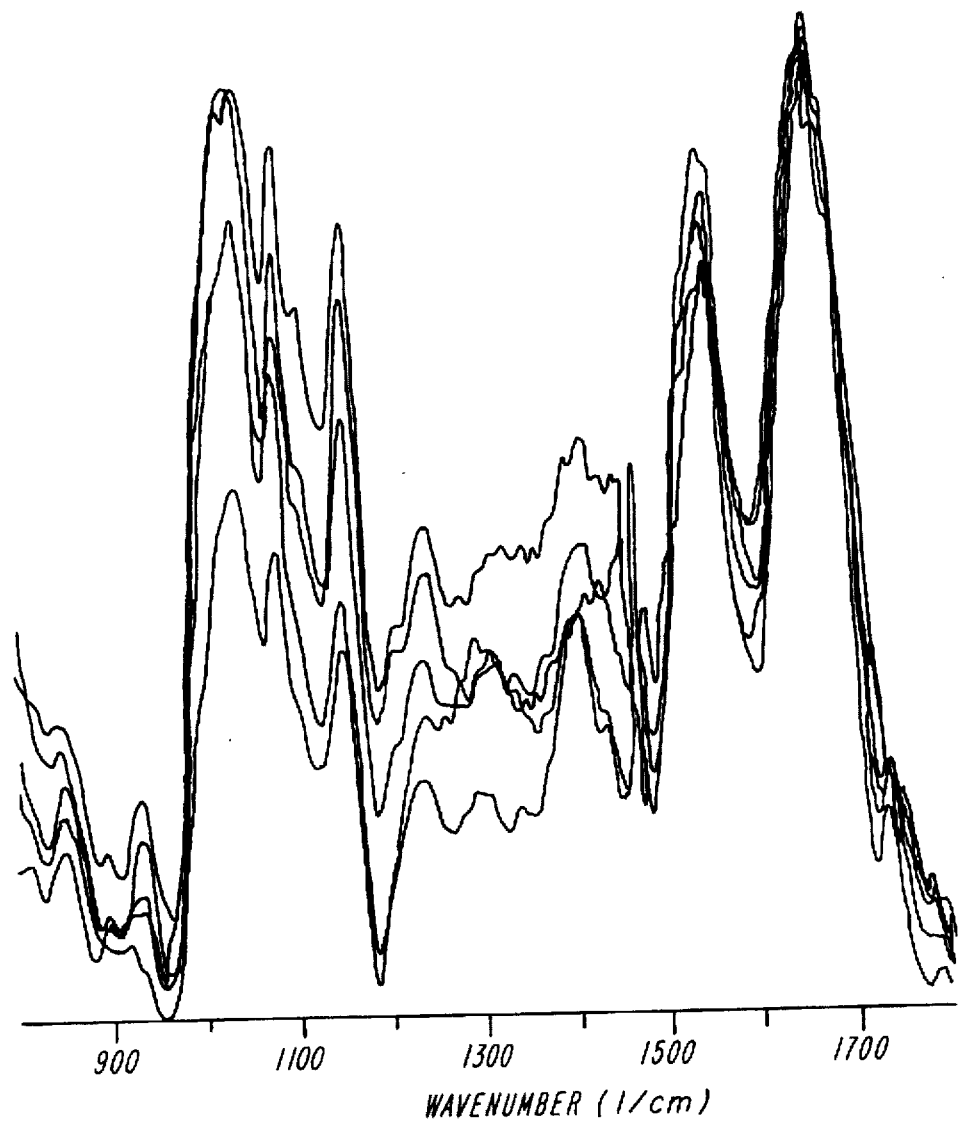
FIG. 3 shows infrared spectra of cervical cells for woman patients who have no disease of the cervix.

Referring to FIG. 3, several infrared spectra of cervical cells are shown for women patients who have no disease of the cervix. The index cases (lowest three spectra for example) are from women patients whose colposcopic examinations of the cervix were normal and who had biopsies of the exo- and endocervix that also were normal. The cervical cells obtained from these women, by the standard method of the PAP smear from scraping cells from the endo- and exocervix, were normal and the infrared spectra of these cells also showed them to be normal.

The details of the infrared spectra of the index cases are used to determine if a given specimen of cells has infrared properties corresponding to normal cells or cells with evidence of disease. This spectra relates to cells from women whose standard cytology of the cervical cells was interpreted to be normal and the spectra matched the details of the spectra for the index cases.

Following the present invention, what is shown in FIG. 3 are spectra that are essentially identical to each other. Thus, for normal cells, the frequencies, bandwidths, and intensifies of vibrations fall within a narrow range for all women with normal cells. This should be known because, as will be shown, there is considerable patient to patient variation in the spectra of diseased cells when such patients are affected by the same disease. The histopathological record of a patient will show that even slight variation of a patient's condition from another patient may be recognized because of the discrimination that is possible using the present invention.

Figure 4:
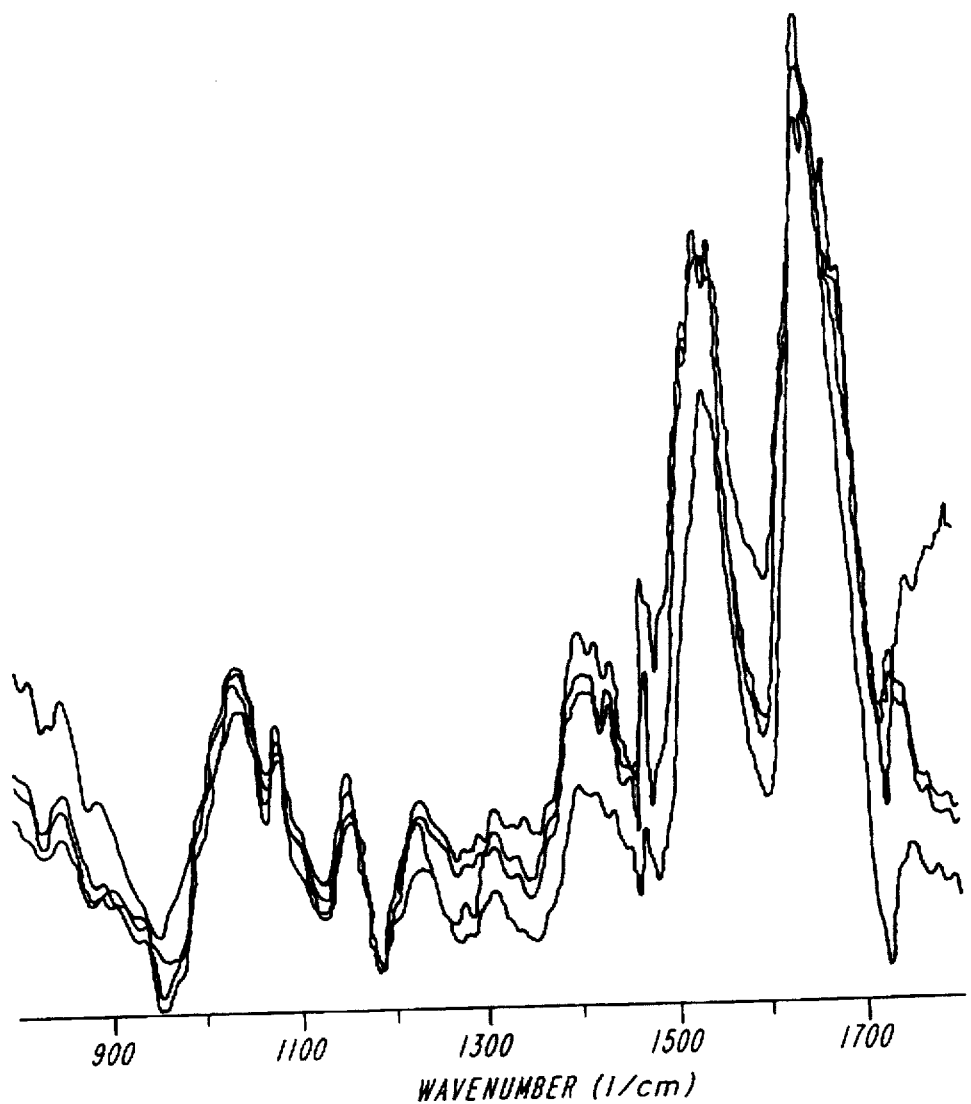
FIG. 4 shows infrared spectra for a number of woman that have cervical cells diagnosed as normal cells.

Referring to FIG. 4, infrared spectra from women with cervical cells diagnosed as normal by cytological examination of cervical cells is shown. A comparison of the spectra in FIG. 4 with any spectra in FIG. 3 will show that the spectra in FIG. 4 diverge from the constancy of features among the infrared spectra in FIG. 3. The spectra in FIG. 4 are not characteristic of cervical cells with dysplasia, as detected by histopathological examination of cervical biopsies. Rather, the spectra in FIG. 4 diverge from the normal in FIG. 3 in the same qualitative way as spectra of mildly dysplastic cells. As such, the infrared spectra in FIG. 4 are for cells that are beginning to accumulate errors in their DNA but do not as of yet display morphologic evidence of dysplasia. This provides an example of the discrimination possible using the present invention, in which infrared spectroscopy is able to be used to detect differences in cells that are undetectable by any other means and method.

The present invention has applicability for detecting difference in other than cervical cells. For example, the present invention may use its method of infrared spectroscopy to detect the presence of abnormalities in cells that are below the level of detection by microscopic examination of cells and/or tissues. Referring to FIGS. 5 to 7, the presence of those abnormalities in cells will be explained.

Figure 5A:
FIG. 5A shows a representation of a cytologic PAP smear of cervical cells that has been interpreted as displaying normal epithelial cells but a larger than normal number of acute inflammatory cells.

FIG. 5A shows a cytologic PAP smear of cervical cells that has been interpreted as displaying normal epithelial cells but a larger than normal number of acute inflammatory cells. The large cells in FIGS. 5A are the epithelial cells. The corresponding infrared spectrum, in the range of frequencies displayed in FIGS. 3 and 4, is displayed in FIG. 5B. The spectrum in 5B is different from that for normal cervical epithelial cells. This is contained by comparing the spectra in FIG. 3 with that in FIG. 5B.

Figure 5B:
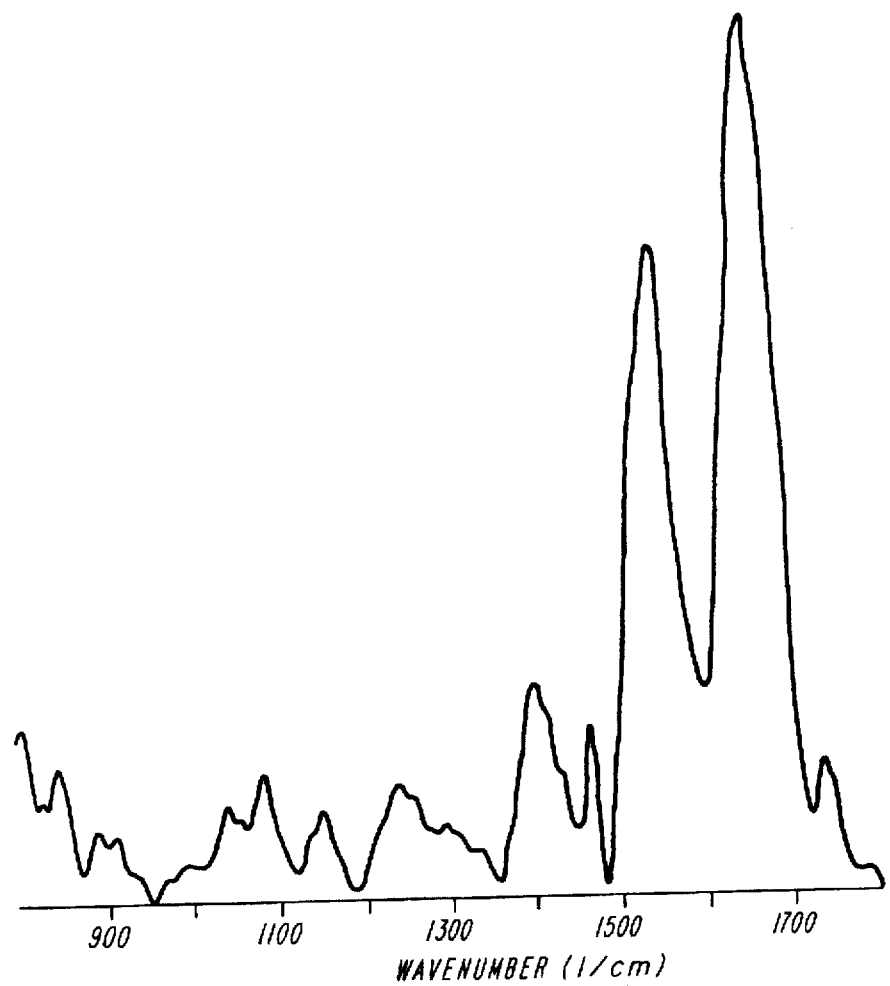
FIG. 5B shows the infrared spectra of the cells in the cytologic smear in FIG. 5A.
Figure 6A:
FIG. 6A shows a cytologic smear of cervical cells that were interpreted as being normal and showing a normal number of active inflammatory cell.
Figure 6B:
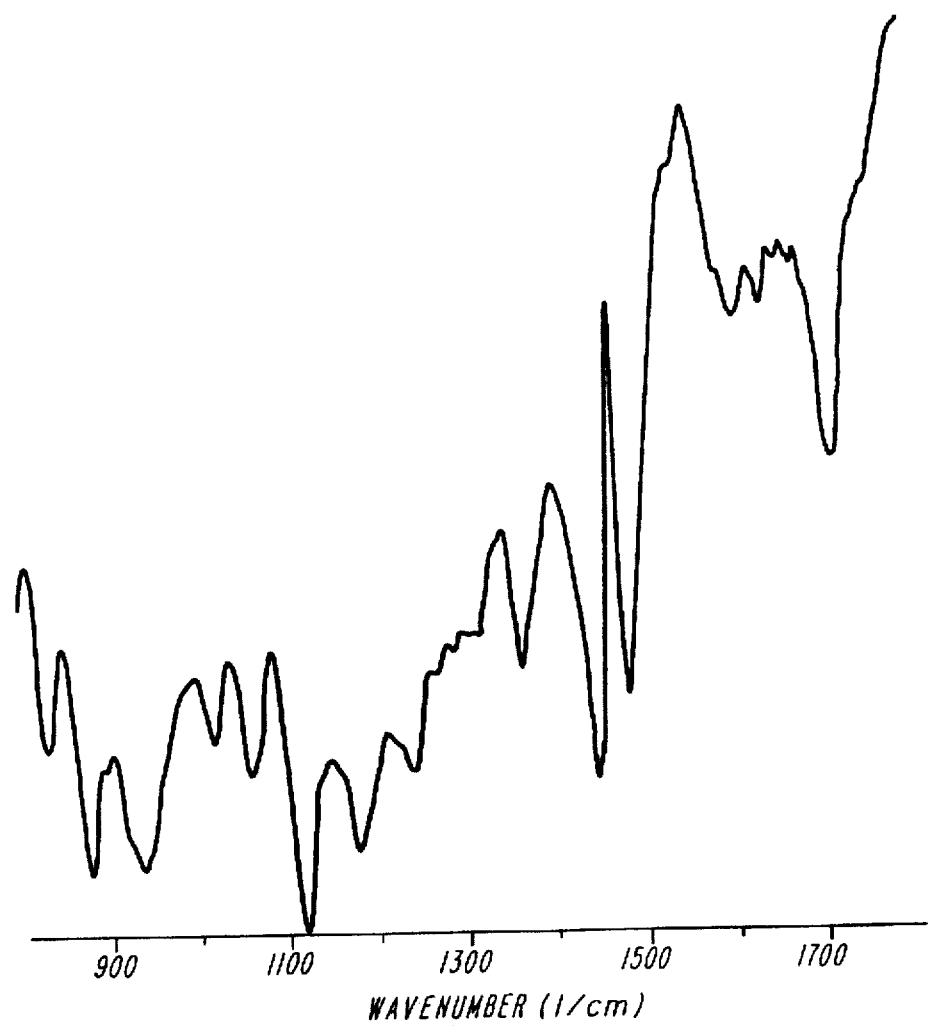
FIG. 6B shows the infrared spectrum of the cytologic smear of cervical cells shown in FIG. 6A.
Figure 7:
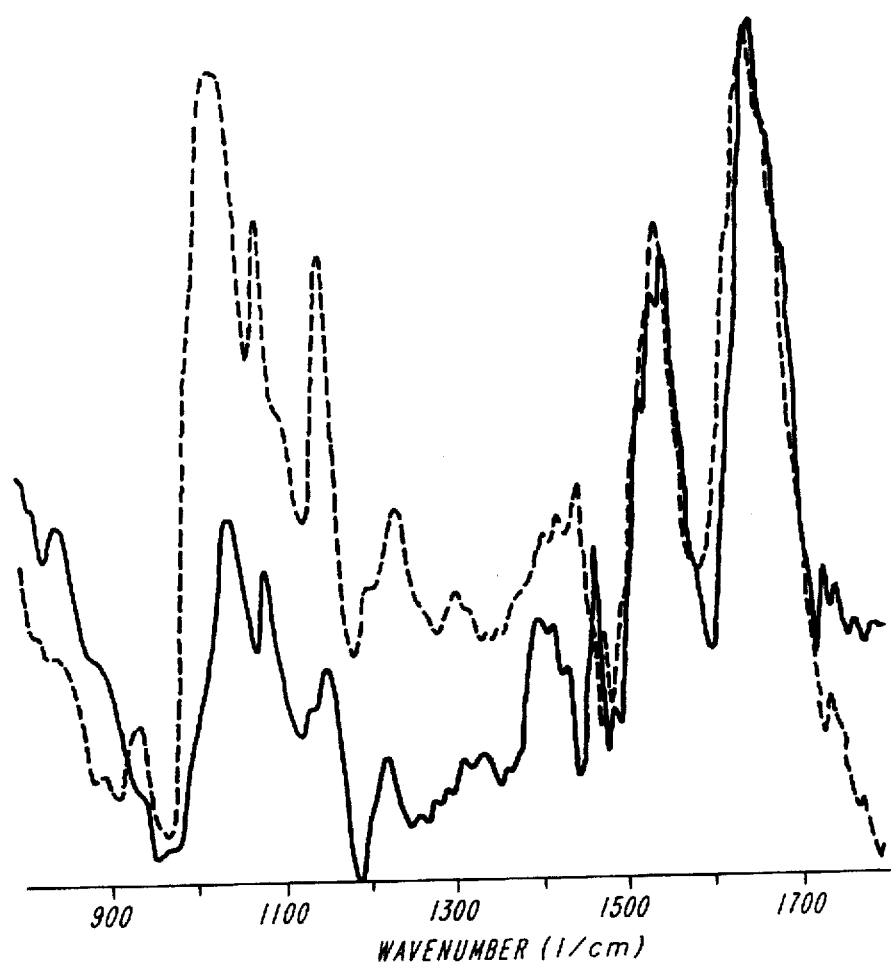
FIG. 7 shows the infrared spectra of cervical cells corresponding to normal cells (dashed line) and cells with CIN I (solid line).

FIG. 6A shows a cytologic smear of another specimen of cervical cells. The epithelial cells in this smear were interpreted to be normal, but the sample was diagnosed to contain an abnormally large number of acute inflammatory cells, the small cells in the figure. The infrared spectrum of the epithelial cells in FIG. 6A is shown in FIG. 6B. By comparison with the spectra in FIG. 4, the epithelial cells in FIGS. 5B and 6B are not normal.

Viewing the smears and spectra in FIGS. 5A and 6A demonstrates the advantages of infrared spectroscopy versus histopathological methods of detecting disease in cells. First, the infrared spectroscopic method detects disease that is undetectable by a microscopic study of cells. This is readily seen in that the epithelial cells in FIGS. 5A and 6A appear normal under the microscope but infrared spectroscopy of these cells in FIGS. 5B and 6B shows the presence of disease, as reflected by the abnormal vibrational bands for the molecules within the cells.

The spectra in FIGS. 5B and 6B cannot be generated by summation of spectra for normal epithelial cells plus the spectra for other types of cells because of the disappearance of prominent vibrational bands due to normal epithelial cells. Therefore, the spectra in FIGS. 5B and 6B reflect changes in the vibrational bands of the epithelial cells.

The present invention will now be used to show that infrared spectroscopy will detect a well-characterized disease in cells that also is often below the level of detection by microscopic examination of cells.

A cytologic smear of cervical cells is interpreted as showing dysplasia of any grade, e.g., grade I or CIN I when at least one cell on the entire smear has the characteristics of dysplasia. Typically, smears diagnosed as dysplasia have between one and five to ten dysplastic-appearing cells, on the basis of microscopic examination, in a population of thousands of normal-appearing cells.

An infrared spectrum of a sample of cells with dysplasia is shown in FIG. 7, in the solid line. The dashed line is the spectrum of normal cells shown for reference. Diagnosis for both samples of cells were confirmed by colposcopy and biopsy of cervical tissues. Comparison of the dysplastic and normal spectra in FIG. 7 shows that the spectrum of the dysplastic specimen cannot be reconstructed from the spectrum of the normal cells plus any other type of spectrum and therefore that nearly all the cells, not a minority of the cells, display infrared characteristics of dysplasia. That is, when dysplasia is present in a smear of cervical cells, the infrared spectrum of the cells shows that, in contrast with the microscopic method in the presence of dysplasia, the infrared method detects that essentially all the cells in a sample are dysplastic and that there are few if any normal cells present, using the criteria of normality by infrared examination of the cells. Contrary to the results of cytology and current beliefs for grading the extent to which cells have evolved from normal to dysplasia to cancer, the present invention and its use of infrared spectroscopy shows that nearly all the cells in the sample examined are dysplastic to some degree. This follows from reconstruction of spectra based on mixing the spectral features of normal and dysplastic cells. The abnormal spectrum in FIG. 7 can be reconstructed only in the case that the sample contains a very small proportion of normal cells.

The infrared spectroscopic examination and analysis of cells detects a level of precancer in cells that is usually undetectable by microscopic examination of such cells. As indicated, standard pathological methods determine that only a small minority of cells are affected with dysplasia in smears, while the infrared spectroscopic method of the present invention detects that essentially all the cells are affected with dysplasia in one way or another.

Although there am well-known problems in the acquisition of samples for PAP smears and large variations in the skill levels of the examiners, the present invention demonstrates that heretofore there were inherent limitations in the fundamental technique of detecting dysplasia on the basis of microscopic examination of cells. These limitations, however, am overcome by collecting information about cells via vibrational spectroscopy. That is, extensive changes in the chemical and physical attributes at the molecular level in cells may not appear as changes in the morphology of the cells, but these changes are detected by vibrational spectroscopic examination of the cells. The showing that infrared spectroscopy of cervical cells detects dysplastic, precancerous disease in cells that appear normal morphologically explains why cervical cancer appears to develop rapidly in some patients without the evolution through the stages of dysplasia. It also accounts for why as many as ⅓ of patients with invasive cancer of the cervix have had a normal PAP smear within about one year of diagnosis of cancer, and why the PAP smears do not detect all patients with cervical dysplasia.

Figure 8A:
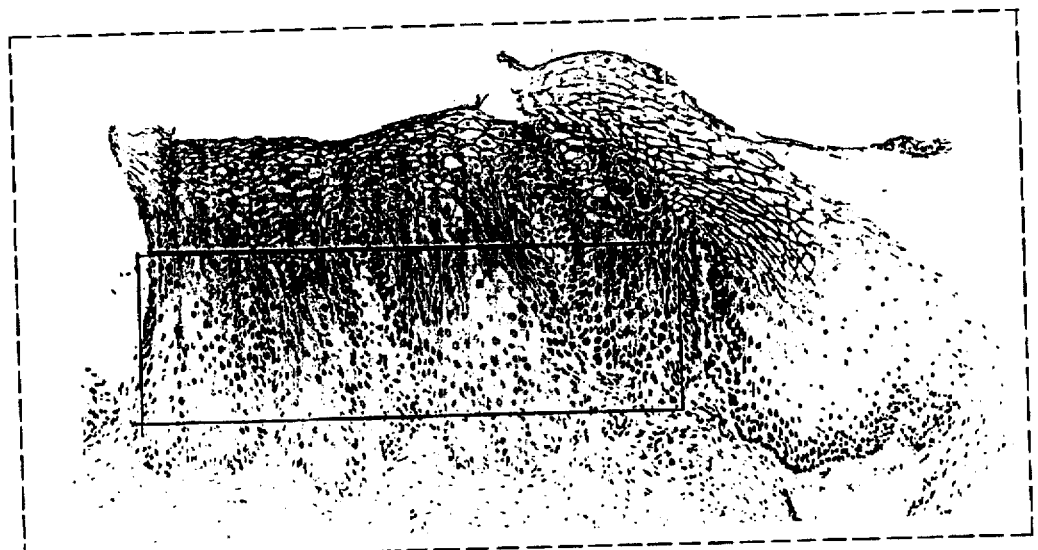
FIG. 8A shows a cervical biopsy of the exo-cervix which was interpreted as showing mild dysplasia (grade I or CIN I).

The discrepancy between the detection of disease by cytology versus vibrational spectroscopy extends to a comparison of microscopic examination of biopsies versus examination of cervical cells by infrared spectroscopy. FIG. 8A shows a cervical biopsy of the exocervix. The biopsy Was interpreted as showing foci of mild dysplasia (grade I or CIN I). The abnormal cells are indicated within the box. With regard to the interpretation of the biopsy, the distribution between normal and diseased cells in the biopsy in FIG. 8A shows primarily normal cells and histopathological criteria, and the degree of abnormality of the diseased cells was interpreted as mild, or early in the progression of the cells from normal to cancer.

Figure 8B:
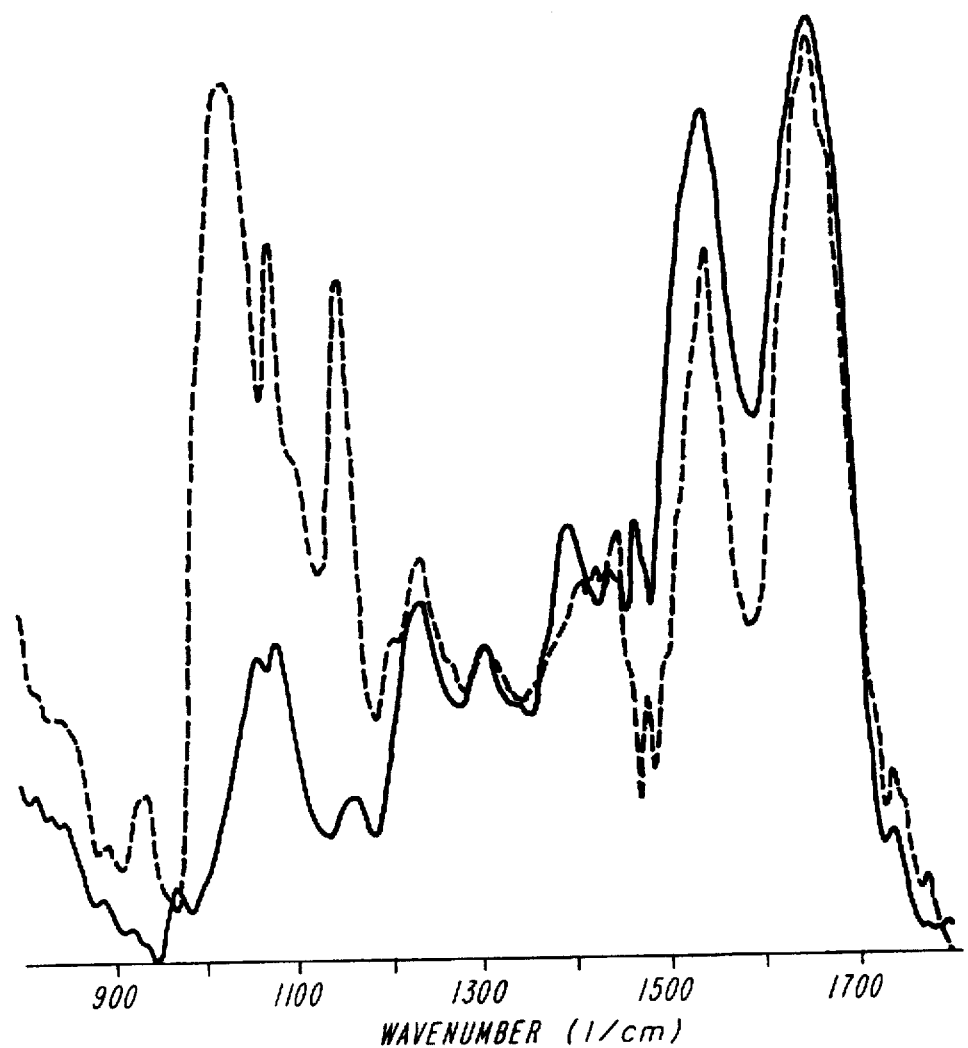
FIG. 8B shows the infrared spectra of cervical cells collected from a patient before the biopsy in FIG. 8A was obtained.

FIG. 8B shows the infrared spectra of cervical cells collected from the patient immediately before the biopsy was obtained. The spectra does not reflect the presence of a mixture of normal cells and diseased cells, except in the case that the percentage of normal cells was quite small. This spectra teaches, therefore, that nearly all the cells collected in the sample of cervical cells scraped from the patient, immediately prior to biopsy of the same cells, were diseased. As will be shown, the spectral features in FIG. 8B correspond to cells with dysplasia (or precancer) more advanced than mild or grade I (CIN I). The conclusion to be drawn from these examples is the same as those from the example in FIGS. 5A–7. Microscopy of tissue, as compared with infrared spectroscopy, does not detect the true number of cells affected by dysplasia or the extent of progress of precancer to cancer.

Referring to FIGS. 3–8B, the following applies: (i) Cells can be normal histopathologically but minimally deviated from normal, as reflected by the infrared spectra of cells in FIG. 3 versus those in FIG. 4; (ii) the present invention has increased sensitivity by the inclusion of the infrared spectral method for finding disease in cells which demonstrate the imprecision of the histopathological methods; (iii) cells determined to be normal histopathologically can be affected with advanced precancerous disease as would be discovered by infrared spectral examination of the same cells; (iv) the discriminant capacity of infrared spectroscopy and other modes of vibrational spectroscopy is greater than cytologic or histopathologic methods for detecting disease in cells and tissues; (v) microscopic examination of cells is no longer a sufficient basis for correlating the clinical stage and course of disease with disease at the cellular level because infrared spectroscopy and other modes of vibrational spectroscopy surpass microscopy in detecting disease in cells; and (vi) infrared spectroscopy will allow the clinician to detect disease in cells to follow the evolution of disease through the various levels of dysplasia.

Detecting and Grading

An experienced pathologist or cytologist should have little difficulty in the histopathologic diagnosis of cancer given sufficient information. The issue then becomes the problem of determining the stage of dysplasia or precancer. As already mentioned, the present invention through the use of infrared spectroscopy is able to track the evolution of cancer cells between normal and cancer cells at a higher level of detection than afforded by morphological changes in cells, through changes in the relationships of different organelles in cells, changes in their relative sizes, and changes in their staining properties.

Prior to detecting and grading, the samples must be collected. Once collection has taken place, then detection of dysplasia is performed. The conventional method of doing this is by microscopic examination of the cells, which has the problems discussed above. If dysplasia is found, the diagnosis generally is that the cell is precancerous. However, this is where the analysis generally ends.

Figure 9:
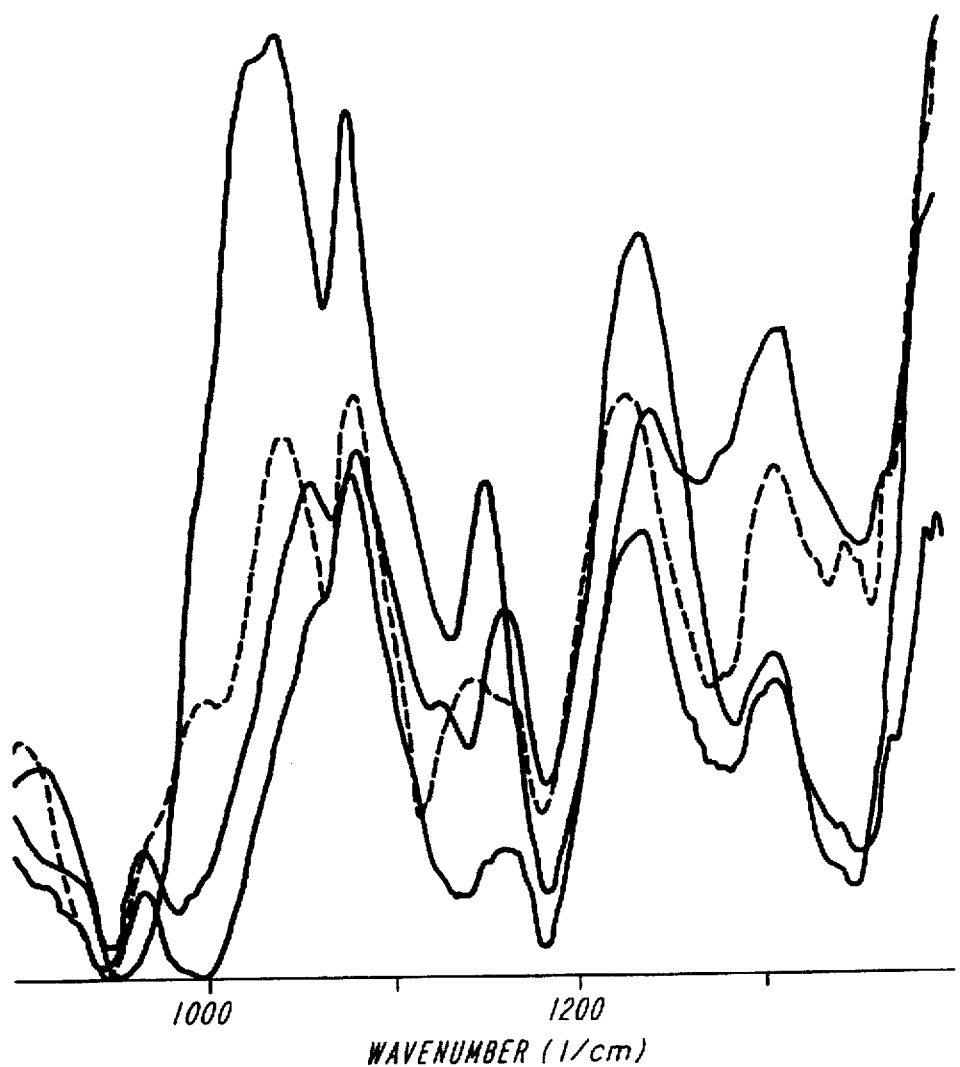
FIG. 9 shows several infrared spectra from patients with dysplasia of the cervix.

Referring to FIG. 9, several spectra from patients with dysplastic disease of the cervix as determined by examination of biopsies of the endo- and exocervix are shown. The spectra that are shown are samples of cervical cells obtained by the usual PAP smear technique immediately prior to cervical biopsy. In FIG. 9, the top spectrum in the stacked plot is a normal spectrum and the remaining spectra are stacked with the least dysplastic tissue at the top and the most dysplastic at the bottom. This relationship of the curves shows the evolution of several spectral features as the degree of dysplasia increases. It is this type of information that microscopic examination fails to provide and does not permit it to truly grade dysplasia.

More specifically in referring to FIG. 9, the changes evolving across the spectra begin with decreasing intensity in the band at 1025 $cm^{-1}$, increasing intensity in the bands at 1040 $cm^{-1}$ and 1050–1054 $cm^{-1}$. These changes are not found in the normal spectra. The net result of these changes is first to broaden the bandwidth of the first spectral band and to shift the center frequency of this band to higher frequency. In addition, there is the intensity increase in the band at 1078 $cm^{-1}$. These effects cause a change in which the spectrum of dysplastic samples have a picket fence appearance at the first two peaks. With further evolution of the spectra, the band at 1078 $cm^{-1}$ shifts to a higher frequency and this band becomes the most prominent peak in the spectrum between about 1000 $cm^{-1}$ and 1100 $cm^{-1}$.

At higher degrees of dysplasia, the first band in the spectrum is broad and featureless; even the bands at about 1040 $cm^{-1}$ and 1054 $cm^{-1}$. These bands, however, grow in intensity as cells become dysplastic and become enveloped by the first featureless band.

The spectral changes as cells evolve from normal through the various stages of dysplasia are not limited to the region between 1000 $cm^{-1}$ and about 1100 $cm^{-1}$. As is seen by viewing FIG. 9, the shoulder at 1103 $cm^{-1}$ of the normal spectra disappears, and at 1151 $cm^{-1}$, there is a broadening of the peak, decrease in intensity, and the center frequency shifts to a higher value. Just above 1200 $cm^{-1}$, the spectrum increases in intensity and the envelope of this band in the spectra from dysplastic cells changes in shape. This band also becomes more prominent than the band at about 1300 $cm^{-1}$ and shifts its center of gravity, ultimately, to a lower value.

There is variability from spectrum to spectrum in the contributions of different vibrations to the envelop of this band in different patients. This is seen in the relative intensities of bands at about 1230, 1300 and 1400 $cm^{-1}$, which change in a continuous way as dysplasia increases. The first two bands, which increase in intensity with the onset of dysplasia, are of about equal intensity in low grades of dysplasia. This relationship changes as dysplasia increases. Specifically, the intensity of the band at 1230 $cm^{-1}$ becomes greater than the intensity of the band at about 1300 $cm^{-1}$. Of these changes, the shift in the peak of the band normally at 1235 $cm^{-1}$ is the most variable of the changes associated with dysplasia and the least useful for determining the stage of evolution from normal to cancer cell. The significance of the variable change in the frequency of the peak of the vibration normally at 1235 $cm^{-1}$, will be discussed in detail subsequently.

Figure 10:
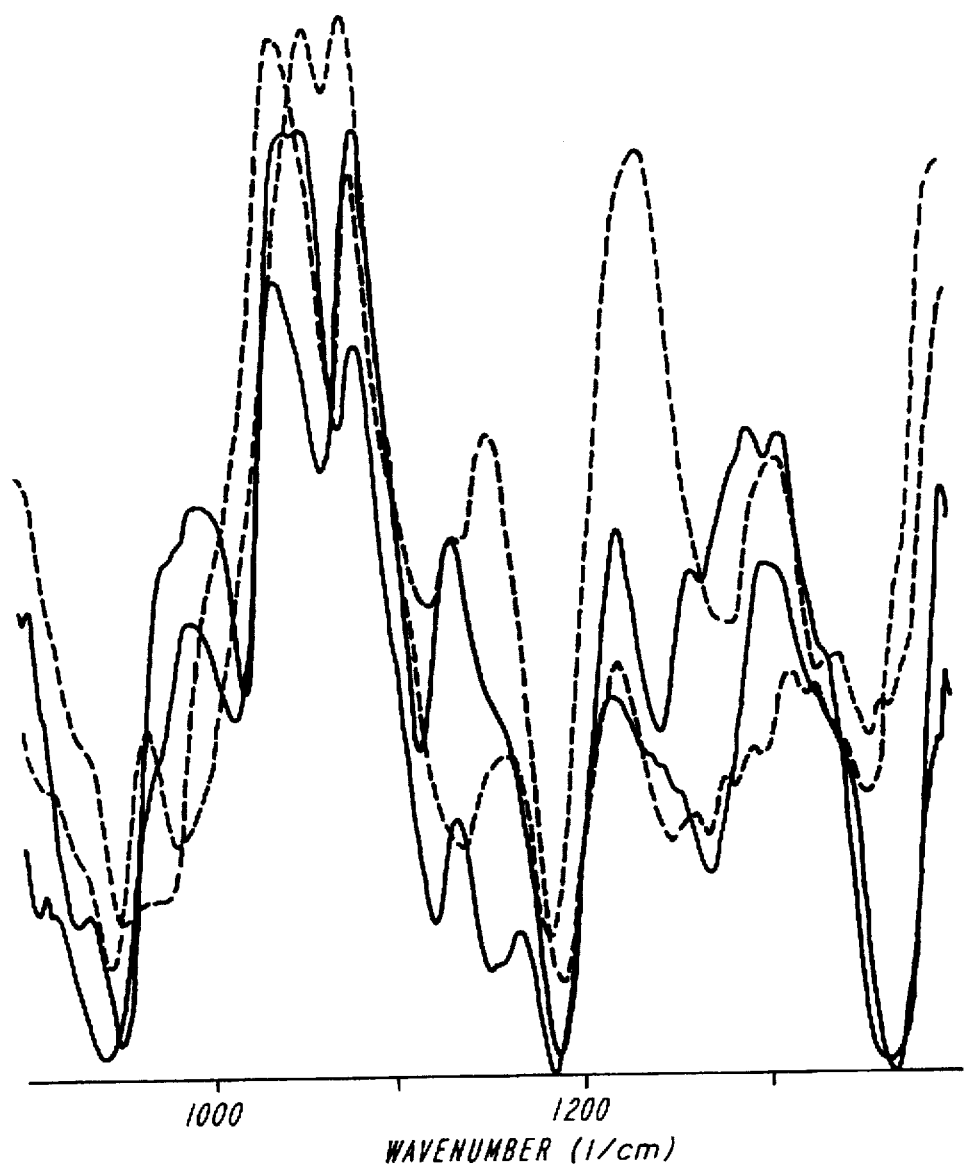
FIG. 10 shows infrared spectra from patients with histopathological diagnoses of dysplasia made based on cervical biopsies.

FIG. 10 shows spectra from patients in whom histopathological diagnoses of dysplasia were made on the basis of cervical biopsies. A comparison of FIGS. 9 and 10 show that there are similarities between the spectra in the two Figures, especially with regard to changes in spectral bands around 1000 cm$^{-1}$. However, the spectra in FIG. 10 has a different evolution pattern through stages of dysplasia. The main differences between the series of spectra in FIG. 9 and FIG. 10 include the following: (i) the appearance of a band at about 1000 cm$^{-1}$ for the spectra in FIG. 10; (ii) a downward shift in the frequency of the band normally at 1151 cm$^{-1}$; (iii) the apparent "splitting" of this band into two bands as dysplasia increases so that there are recognizable independent maxima on the low and high frequency side of the normal single maximum at 1151 cm$^{-1}$, e.g., a peak at about 1135 cm$^{-1}$ and another at about 1160 cm$^{-1}$ or higher; (iv) as compared with the spectra in FIG. 8, the envelope of the band normally at 1233 cm$^{-1}$ has an especially prominent maximum at an unusually small wave number in FIG. 10; (v) the relative intensifies of the peaks at about 1235 cm$^{-1}$, 1310 cm$^{-1}$, and 1410 cm$^{-1}$ that are different from normal as well as different from the series of spectra in FIG. 9. Even in light of these differences, the series of spectra in FIG. 10 show a progression of changes consistent with the progress of a disease, but different in detail from the progressive changes in the spectra in the series in FIG. 9. This detection is provided because of the use of vibrational spectroscopy as set forth in the present invention.

Figure 11:
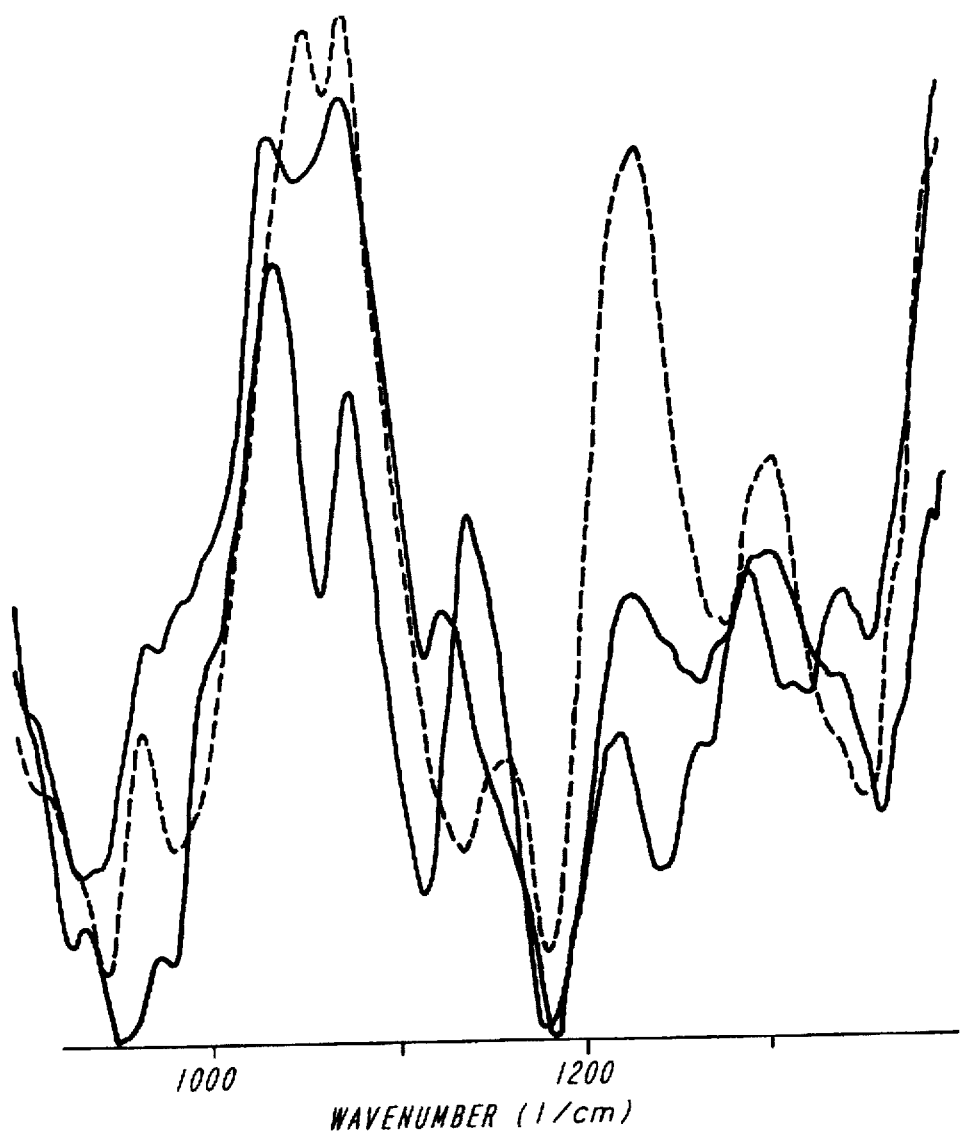
FIG. 11 shows the infrared spectra of samples from patients with dysplasia in biopsies of the cervix and evidence of the infection with human papilloma virus ("HPV").

Referring to FIG. 11, spectra of samples from patients with dysplasia in biopsies of the cervix and evidence, microscopically, of infection with human (HPV) papilloma virus are shown. The spectra in this series of dysplastic samples are different from normal spectra and different from the series of spectra in the dysplasia displayed in FIGS. 9 and 10. The distinguishing features of the series of spectra in FIG. 11 are as follows: (i) these spectra have a peak at 970 cm$^{-1}$ and this peak is not intense and is similar in intensity to the peak at about 965 cm$^{-1}$ in the dysplastic spectra in FIGS. 9 and 10; (ii) the spectra in FIG. 11 have a signature region between about 750 cm$^{-1}$ and 950 cm$^{-1}$ (which is shown in detail in FIG. 12). The band at 970 cm$^{-1}$ and the signature region of the spectrum for dysplasia plus HPV, for the region below 950 cm$^{-1}$, are characteristic of cells infected with HPV; (iii) there are unusually advanced changes in the region of the spectra between above 1000 cm$^{-1}$ and 1100 cm$^{-1}$ as compared to histopathological grades of dysplasia. The lowest traces in FIG. 11, for example, were diagnosed as mild dysplasia on biopsy of the cervix. The spectra show a complete disappearance of the normal band at 1025 cm$^{-1}$, which occurs for the series of spectra in FIGS. 9 and 10 only at more advanced stages of dysplasia. It is important, however, that the spectra in FIG. 11 share important features with the series of dysplastic spectra in FIG. 10, as for example, a band at about 1000 cm$^{-1}$, a splitting of the normal peak at 1151 cm$^{-1}$, a relationship between the peaks at 1235 cm$^{-1}$, 1310 cm$^{-1}$, and 1410 cm$^{-1}$ that is unlike the pattern in FIG. 9, including the occurrence of the 1235 cm$^{-1}$ peak at unusually low frequencies and with low intensity.

Figure 12:
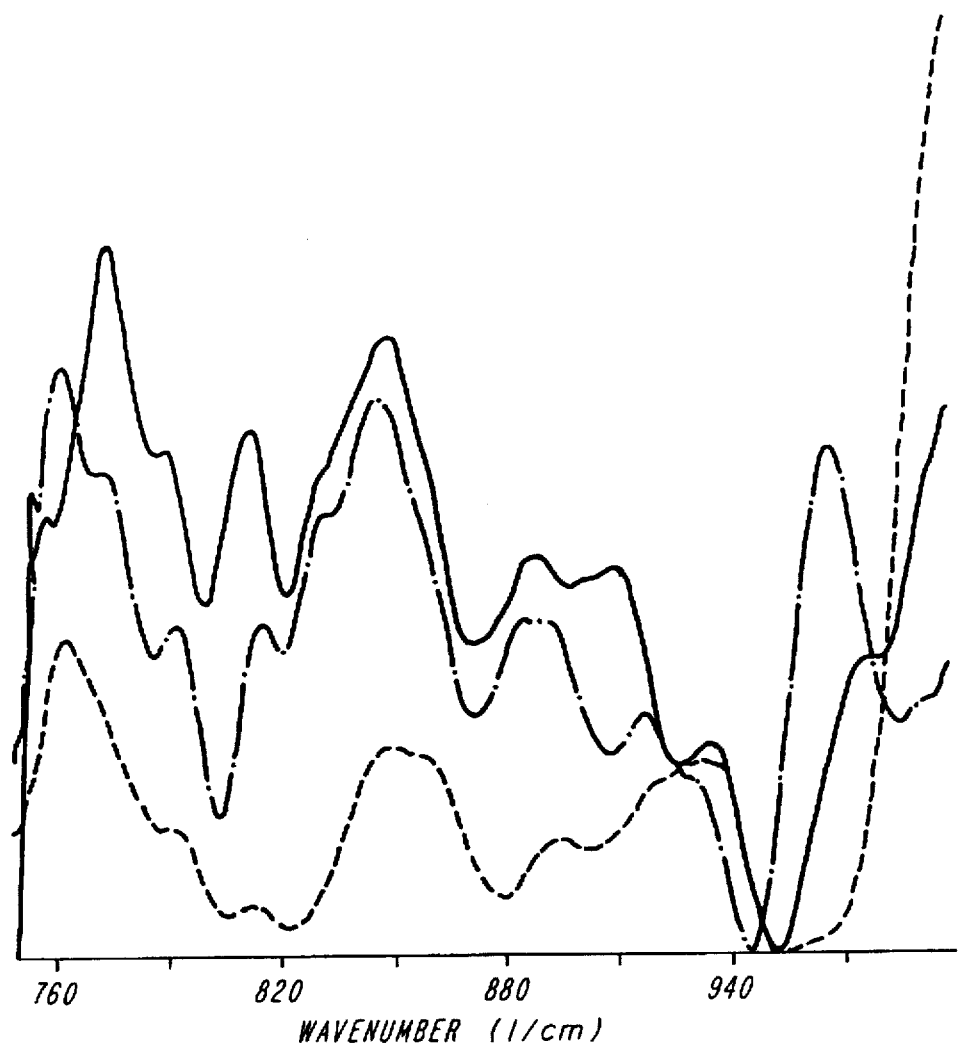
FIG. 12 shows the infrared spectrum of cervical cells with histological evidence of HPV infection (solid line), in the spectral region of 750–1000 $cm^{-1}$.

Referring to FIG. 12 the spectrum in the solid line is of dysplastic cells with histological features of HPV infection. The spectrum in the alternating dots and dashes is of dysplastic cells without histological evidence of HPV infection. The spectrum in the dashed line is of normal cells.

Figure 2:
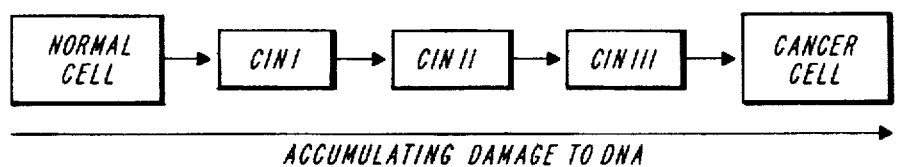
FIG. 2 shows the pathologists' concept for the evolution of normal cells to cancerous cells.

The examples in FIGS. 8-12, show spectra that were generated using infrared spectroscopy. The use of the infrared method shows at least three patterns by which dysplasia evolves. This is not meant to suggest that these are the only patterns. In fact, there can be numerous patterns that result in the evolution of dysplasia as shown in FIG. 1. The evolution of dysplasia shown in FIGS. 8-12 also is contrary to current thinking about the process of dysplasia being a linear change along a single path (FIG. 2). In fact, what FIGS. 8-12 do show is the way infrared spectra of dysplastic cells change and the way the process of dysplasia moves along several different pathways (FIG. 1). The multiple paths in FIG. 1 are detectable as different patterns of dysplasia in cells via the application of infrared spectroscopy to the diagnostic process but not by microscopic examination of cells.

The infrared spectra in FIGS. 8-12, according to the present invention, show the ability to track the evolution of diseased cells through stages of dysplasia. This involves both large and minute changes which result in the number of stages of dysplasia that can be detected rather than the current classification of the three CIN grades I, II, and III.

Another spectral example which summarizes the clinical utility of infrared spectroscopy as a detection tool in cervical cells is the following, which make reference to Table 4 below.

TABLE 4

| PATIENT # | PAP SMEAR | CERVICAL BIOPSY | SPECTRA ANALYSIS OF CELLS |
|---|---|---|---|
| PATIENT 1 | NEGATIVE | CIN II; HPV | CIN V, HPV |
| PATIENT 2 | NEGATIVE | CIN I | CIN II–III |
| PATIENT 3 | NEGATIVE | CIN I (MILD) | CIN II–III |
| PATIENT 4 | NEGATIVE | CIN I | CIN I |
| PATIENT 5 | NEGATIVE;? HPV | CINI | CIN II HPV |
| PATIENT 6 | NEGATIVE | CIN I | CIN I |
| PATIENT 7 | NEGATIVE | CIN I | CIN II |
| PATIENT 8 | MILD ATYPIA RECOMMEND COLPOSCOPY | NO DYSPLASIA | NEGATVE |
| PATIENT 9 | ATYPIA | N.D. (PREGNANT) | CIN II |
| PATIENT 9A | INFLAM. ATYPIA | CIN I | CIN I |
| PATIENT 10 | ASCUS | ATYPIA NO DYSPLASIA | ABNORMAL; POSSIBLE CIN I–II |
| PATIENT 11 | ASCUS | CIN I; HPV | CIN I; HPV |
| PATIENT 12 | ASCUS | CIN III | CIN II |
| PATIENT 13 | ASCUS; RULE OUT CIN I | CIN I | CIN I |
| PATIENT 14 | ASCUS | CIN I–II | CIN; HPV |
| PATIENT 15 | ASCUS | CIN I | CIN I–II |
| PATIENT 16 | ASCUS | NUCLEAR | CIN I–II |

TABLE 4-continued

| PATIENT # | PAP SMEAR | CERVICAL BIOPSY | SPECTRA ANALYSIS OF CELLS |
|---|---|---|---|
| | | ATYPIA | |
| PATIENT 17 | ASCUS | CIN I; HPV | CIN II |
| PATIENT 18 | ASCUS | CIN I | CIN II |
| PATIENT 19 | ASCUS | CIN II | CIN II |
| PATIENT 20 | ASCUS | CIN I; HPV | CIN I–II |
| PATIENT 21 | ASCUS | INFLAMATION | ABNORMAL |
| PATIENT 22 | CIN I–II | NO DYSPLASIA | NO DYSPLASIA |
| PATIENT 23 | CIN I | CIN I; HPV | CIN I; HPV |
| PATIENT 24 | CIN I;? HPV | CIN I; HPV | CIN I; HPV |
| PATIENT 25 | NEGATIVE | NEGATIVE | NEGATIVE |
| PATIENT 26 | CIN I; HPV | CIN I;? HPV | CIN II |

Table 4 includes results for 27 women and that compares the diagnoses made by PAP smear, biopsy of the cervix, and infrared spectroscopy of cervical cells collected immediately before cervical biopsies were obtained. According to Table 4, there is a poor correlation between the cytological diagnosis and the biopsy diagnosis. Specifically, the cytological diagnosis and the biopsy diagnosis were in agreement in only 4 of 27 patients. This confirms the result shown in Table 1. The cytological diagnosis failed to detect significant dysplasia in 18 of 27 patients with dysplasia. Of these, 6 patients with biopsy-proven dysplasia were determined to be normal by cytological diagnosis. The cytological method misdiagnosed dysplasia in 3 of 4 patients with no significant cervical disease In contrast, the infrared method applied to cervical cells detected all patients with dysplasia based on the histopathology of cervical biopsies. The infrared method detected normal cervical cells in all patients misdiagnosed as disease by cytology. The diagnoses based on infrared spectroscopy of cervical cells differed from the biopsy diagnosis in regard to the degree of dysplasia. In most instances, the infrared method diagnosed the dysplasia to be more severe than the histopathology grade of dysplasia.

Table 4 demonstrates that infrared spectroscopy according to the present invention provides information regarding the condition of cells that heretofore was not available. This extends to both the detection and the grading of levels of dysplasia. Moreover, the infrared method can provide better more consistent results than histopathological examination of cervical biopsies for the purposes of detecting the presence or absence of significant cervical disease, e.g., dysplasia, and for grading the degree of any dysplasia found. As such, the infrared spectroscopy method provides accurate information with regard to cells as they are evolving from normal to cancer cells by examination of these cells alone, detection that cells are evolving from normal states through stages of precancerous states by different specific pathways, detection of the presence of human papilloma viral infection of cells, quantitative meaning to the extent of dysplasia in cells, and a means to identify patients who are progressing rapidly to cancer. It also provides a means for detecting and quantitating the extent and rate of progression of precancerous disease to cancer on the basis of serial examinations of cervical cells from a patient which allows for real-time tracking of the disease, a means that allows clinical decisions to be made on the basis of quantifiable changes, or lack thereof, in the extent and rate of progress of precancerous disease, and a means for determining on a real-time basis the efficacy of agents to inhibit and/or prevent the progression of precancerous disease or that cause these diseases to regress. Further, the present invention provides a method for the immediate diagnosis of cervical disease at the point of care, and an inexpensive method to examine cervical cells by infrared spectroscopy which will replace the expensive procedures of repeated culposcopy and cervical biopsy in the definitive diagnosis, follow-up, and treatment of cervical disease.

Interpretation and Diagnosis

The infrared spectrum of a sample of cells is collected and converted to a digitized form. This provides an objective data set. The infrared spectra thus obtained may be analyzed by the system of the present invention to provide a diagnosis. The system has storage for storing the digitized form of the objective data set. The storage also will include a patient's previous spectra so that the most recent set of objective data can be compared with historical data. These comparisons will permit the system of the present invention to show the extend of changes of the disease in light of prior examinations. Because of the ability to store and recall of digitized sets of prior spectra, any of the prior data sets can be used as a basis for interpreting the significance of the most recent spectral examination of cervical cells. For example, the physician and patient would benefit from knowing whether a state of dysplasia has been stable, advanced, or regressed since the last examination. It also would be highly valuable to be able to measure the rate at which changes in the state of dysplasia have occurred since the prior examination.

This comparison of the spectra data will allow rapid interpretation of the most current data and diagnosis based on the level of dysplasia. Thus, a woman whose prior samples displayed non-normal spectra could keep a close eye on her condition. Moreover, the nature of the data sets obtained from spectral examination of cervical cells makes it possible to reinterpret old spectra whenever sufficient new clinical information (e.g., correlations between spectral data and the clinical behavior of disease states reflected by changes in the vibrational spectra of cells and tissues) adds to the clinically relevant information that can be extracted by machine analysis of a data set.

Analysis of Data Sets

Once a vibrational spectrum of cells or tissue has been obtained according to the present invention, it may be processed for display on a CRT for interpretation. The analysis is begun by applying a Fourier transformation to selected digitized data that have been stored. Preferably, a computer driven infrared spectrometer is used to process, store, and display the digitized data.

The transformed data sets are further processed and analyzed. This analysis will include, but not be limited to, the definition of peaks, bandwidths, deconvolution of peaks, subtraction of one spectrum from another, comparison of one spectrum with another by overlaying two or more spectra so as to determine the changes in patterns as dysplasia increases. This analysis will provide the information which permits diagnosis.

More specifically, a number of different actions may be performed on the collected data sets. These actions can be categorized as analytical testing for establishing a diagnosis. This will include an expansion of spectra to emphasize established regions of highest sensitivity to the presence of disease while suppressing spectra regions containing no useful pathological information.

The regions of interest with regard to cervical cells spans the range from 750 $cm^{-1}$ to 1800 $cm^{-1}$. The spectra are normalized in this region for equal intensity of the carbonyl stretching vibration (1600–1700 $cm^{-1}$). The absolute value of the intensity of the infrared absorption in this region is used to measure the number of cells in a sample and for quality control of the sample.

In analyzing the data sets, the expanded spectra are approximated by a number of Gassing band envelopes. The Gaussian bands will be associated with peaks in the spectra. Since many vibrational transitions occur at the same frequency, a spectrum may be reproduced accurately by fitting 10–25 Gaussian bands to it. The number of Gaussian envelopes depends on the trade off of accuracy and computational time. Appropriate comparisons are made of the Gaussian envelopes to determine stages of dysplasia, classes of dysplasia, and other information.

As an example, in the range of 750–1800 $cm^{-1}$, the absorption spectrum for a sample of cervical cells can be decomposed into about 15 Gaussian envelopes that reproduce the observed spectra to within a few percent. In this matter, a 1000 point spectrum is described by less than 50 parameters, namely intensities, frequencies, and bandwidths of each Gaussian envelope. However, a vibration of weak intensity may that bands of weak intensity are properly weighted in the decomposition phase convey a high level of information about the presence or absence of disease and about the type of disease present in one or another spectrum. Therefore, care is taken to insure that bands of weak intensity are properly weighted in the decomposition phase.

The decomposed Gaussian bands are used to identify the frequencies of bands, the intensity of bands, the bandwidths, and the relationship between intensities of different bands in spectra associated with normal cells and cells that are diseased. Thus, the decomposed Gaussian bands that describe the spectrum of a sample of cells when analyzed provide the disease information regarding the cells at issue in a sample.

A second approach also is possible. According to this approach of the present invention, the entire spectrum is treated as a linear combination of mutually orthogonal functions that bear no intuitive meaning. However, the regions of n-dimensional space defined by the multifunctional analysis of a spectrum indicates the presence or absence of different types of disease reflected by the analysis of the spectrum of a given sample of cells. Additionally, the spectrum of the sample contains information indicative of the extent of the progression of a specific type of disease, as defined by the region of n-dimensional space occupied by the spectrum. This approach has inherent advantages because it treats the entire spectrum in a manner which produces a low error rate in the analysis and allows a classification and ordering of sample spectra with respect to each other.

After the analysis, the next step is diagnosis. A comparison or other evaluation of the data sets will provide the pathologist with the location and types of difference in the frequency spectrum of the most current data set and a historical data set. This analysis will show the degree of dysplasia changes and those noted changes will permit grade the level of dysplasia and as well as provide the diagnosis. The pathologist, based on whether the disease has regressed, remained about the same, or increased, will be able to recommend the proper type of treatment. This will take place not only when in the later stages of the disease, but also at the very earliest stages of the disease, which was before the current methods were able to even detect dysplasia.

The preferred embodiment of the system of the present invention uses infrared/vibrational spectra of human tissues and cells for the purpose of rendering medically useful diagnoses about the presence or absence of disease and the grade level of disease.

This programmed approach can be implemented in a computer with software. This will permit rapid analysis of the data sets for the purpose of determining the level of dysplasia. As such, once the spectra are collected, they can be analyzed on-line by the computer. The analysis can be accomplished by a computer in physical proximity to the optical instrumentation that obtains the data or by a computer at a remote location that is connected to the optical instrumentation.

Construction of Data Bases

The connection between clinical medicine and vibrational spectroscopy, for the purpose of rendering clinically useful diagnoses, is the correlation between the results of standard pathology (which already has proven correlations with clinical diseases) and clinical medicine, with properties of vibrational spectra. As vibrational spectroscopy methods are used in clinical practice, they will first be used to establish a data base that will include information about normal cells, dysplasia cells, and frank cancer cells. A data base of this kind will permit the detection analysis, and diagnosis that is not capable of being performed with current systems and methods. The data base constructed by the system for the method of the present invention can be adjusted for each person even though the same disease will differ some what for each of these people. A basis for correlating disease and normality with a given set or sets of spectral data may be examinations of specimens of the endocervical and exocervical tissues together with clinical examinations of patients and the clinical course of disease.

The vibrational method of the present invention detects disease at earlier stages than the current methods because this method detects abnormalities in the structures of individual molecules that precede development of morphological changes in tissues and cells.

In the context of the evolution of cancer, the most important information is the condition of dysplasia of a cells of each patient a given point in time rather than the comparison of cells with a stored data base. This approach permits the detection of diseases early in their development. Then, the disease's progression with time will provide insight into the significance of changes in the properties of the molecules of cells in each individual patient.

Analysis of a Vibrational Spectrum

The purpose of analysis of the vibrational spectrum of a sample of cells or tissue is to make a diagnosis as to the presence or absence of disease that is medically relevant and, if present, the grade level of the disease. This will provide both the physician and patient with some assurance that either no disease is present or that a diseases in present, the type, and extent of the presence of the disease. The diagnosis must fit with what is known about the genesis and morphology of different diseases, which is the basis for a physician's understanding of the disease and how to treat it. This aspect of the present invention will be explained with respect to the diagnosis of diseases of the cervix. This is meant to be an example and it is understood that this approach would apply to any type of diseased cells.

The classes of diseases of the cervix that are important clinically are precancer or dysplasia (or precancer), and cancer. Since infection with HPV is thought to underlie many cases of dysplasia, the diagnosis of HPV is clinically relevant. These disease states must be discriminated from normal. Also, based on what is shown in FIGS. 3 to 6, there are changes in epithelial cells that represent the presence of disease that can be detected by vibrational spectroscopy but not by current methods. The system of the present invention first screens only the differences between normal and disease. This may be accomplished by comparing a new unknown spectrum with a spectrum from cells known to be normal via a point-by-point subtraction of the normal spectrum from the unknown spectrum. If the resulting difference spectrum is not a flat line, then the unknown is a sample of diseased cells. The criterion that the difference spectrum must be a flat line can be adjusted to account for variability between spectra that are derived from normal cells, i.e., cells not affected with the relevant diseases given above.

Figure 13:
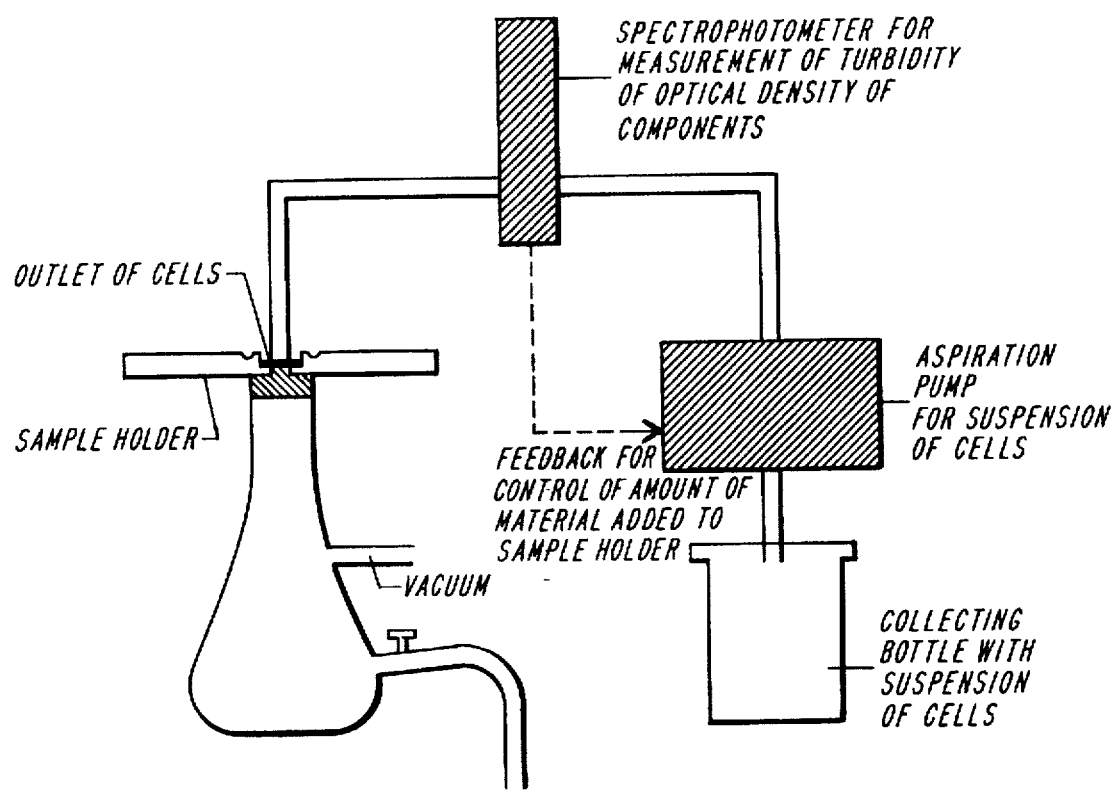
FIG. 13 shows schematically the flow of information for on line analysis of spectral data.

The process of the system of the present invention is shown in FIG. 13.

Classification of Type of Disease Present

Analysis of human tissue in order to make a medically useful and correct diagnosis with the lowest possible chance for error differs from known methods of simply identifying a chemical unknown. The genetic heterogeneity of people plus the varied manifestations of disease can cause variations in the "patterns" of infrared spectra in normal or diseased tissues that do not occur between molecules of a given chemical. The number of possible variations between tissue samples exceeds the number of chemical species that are significant. The number of analyses to be done on unknown tissue samples far exceeds the number of samples that could be used to build a data base on which to base diagnosis on pattern recognition alone.

Although there are spectral differences between different tissue that has the same type of cancer and normal samples of the same tissue, these differences are not significant enough to prevent the use of the overall spectral pattern for comparison which will permit an accurate diagnosis. This diagnosis is only for the purpose of determining the type of disease. This comparison can be simple pattern matching in which a variety of algorithms would give the closest match between the spectrum of an unknown sample and a stored set of spectra in a data base, in which the stored spectra are examples of spectra for different types of disease (of a given type of cell). This data base would also include various grades of disease for each disease type.

This method of classification according to the present invention, provides the classification of the type of disease present based on an analysis of spectra, reduction of spectra by numerical analysis to sets of quantitative diagnostic criteria, with tolerance levels preset in the algorithms, and comparison of derived parameters for an unknown sample with similarly derived numerical parameters for samples known from clinical research to represent the presence of specific types of disease. The analysis and reduction for this purpose can be carried out on the primary data file and/or on several possible difference spectra between the unknown sample and stored spectra known to represent well-defined disease states. The reliability of this classification method may be enhanced by setting parameters for diagnosis that insist on absolute levels of matching between an unknown and a stored spectrum. Analyses that fall out-side predetermined limits are rejected as indeterminate.

As an alternative, an accurate diagnosis will obtain by entering into memory a large number of grades of precancerous disease so that a best match will be within the correct category of diagnosis. This requires that sufficient spectra data be entered into memory to create a continuum of grades of precancerous disease between normal and frank cancer. When the comparison is done, the proper classification will obtain. When this method of diagnosis is used, it creates a basis for a continuum in grading of precancerous disease by taking advantage of the quantitative nature of the fundamental data on which evaluation of cells and tissues is based. In carrying out this method, no attempt is made to match spectra by pattern, rather, a numerical value is assigned by the analytical system to each sample examined so that the degree of precancerous disease is associated with a physical quantity derived from the spectrum of a sample of cells. The quantity represents the deviation of a spectrum in appropriate regions with regard to the spectral parameters such as peaks for given vibrations, peak heights, ratios of peak heights, and bandwidths of peaks, and/or the sum of deviations from a line in a difference spectrum of the unknown and "normal" in the data base that are characteristic of cells with precancerous disease. This analysis is only for spectra deemed to be examples of precancerous disease. The numerical values for the grade of precancer can be made to correspond to linear changes in a given pattern of evolution of dysplasia (FIGS. 6–8, for example), with increasing degrees of precancer.

For the purpose of clinical guidance to physicians, a DYSPLASIA INDEX for a given sample of tissue may be derived in a way that superimposes the DYSPLASIA INDEX on currently used stages of dysplasia identified by histopathology, as for example the commonly used standards of low grade (CIN 1), moderate grade (CIN 2), and high grade (CIN 3) dysplastic disease (FIG. 2). These classifications will give the physician the type of information that he or she will use to seeing so he or she can make immediate therapeutic decisions in the event that an advanced stage of precancerous disease or dysplasia already is present at the first examination of a patient and until physicians become accustomed to using the full capacity of the system and method of the present invention.

A printout of results of the diagnostic analysis may be provided as a graphic representation of the stage of dysplasia by DYSPLASIA INDEX in relation to commonly used criteria for dysplasia (FIGS. 13 and 14). In the event that the patient has had previous examinations of cells and tissues by vibrational spectroscopy, the historical data base will permit a comparison of all previous data base files with the current file in order to determine via the DYSPLASIA INDEX an objective measure of progression or regression of disease. The printout may include a graphical representation of the patient's current status with regard to dysplasia and a separate graphical representation of the time-dependent changes in dysplasia present in samples previously collected and the current sample. This graphical representation is prepared on-line via access to all prior examinations that are contained in a patient's personal records device card.

It is possible via the system of the present invention to identify patients in whom there is rapid progression of the dysplastic disease. This is an especially important group of patients to identify because they have the highest risk of progressing from a dysplastic disease to frank cancer over relatively brief periods of time. Therapeutic decisions have to be made early with respect to such patients, as compared with patients in whom progression is slow. As such, the present invention provides a basis for therapeutic decisions that maximize the benefits to all patients while reducing the total amount of invasive treatment required. Time-dependent changes in the DYSPLASIA INDEX, and the time-derivative of the index, also will be used to monitor responses to chemopreventive therapy that delays progression to cancer and to separate patients in whom mild degrees of dysplasia are static and not threatening.

From the foregoing, it is clear that the system of the present invention converts a subjective process of evaluating pathology to a reproducible, quantitative method that has precise clinical meaning to the physician. The present invention provides quantitative data for the clinician, who then interprets the meaning of this data and who can use this quantitative data to judge the progress of disease, the regression of disease, and the response of disease to therapy. In addition to providing a new basis for determining accurately when patients have precancerous disease, the present invention provides a powerful clinical tool for determining how to treat and when to treat patients with precancerous disease as well as completely new ways for assessing the value of experimental treatments.

Storage of Information

Archival storage of vibrational spectra is accomplished by storing the primary data base file in the computer. This data base file also can be stored on a portable memory device, such as a PCMCIA card (personal records device card), which will permit the patient to take his or her record with them. The personal records device card contains all spectra related to a given patient.

The personal records device card with encoded spectral data allows comparisons of prior and the most current examinations of tissue to be made immediately by the last examining facility whether or not the patient attends the same physician's office, the same hospital, or the same pathology laboratory. Since the patient is the holder of such records, the portable device card will represent all past records at the site of the current examination.

This also can be accomplished by the data file being able to be transmitted to the examining facility by modem. The encoding of spectra on the portable storage machine, together with the basic instrumentation for collecting vibrational spectra and the computer and associated algorithms for analyzing spectra, afford the examining physician the benefit of immediate comparison of current and prior examinations. In the case that diagnostic services are provided at the point of care, the patients need only bring their personal record device card to the physician's office at the time of examination in order to benefit from immediate review of all past examinations. In the case that samples are sent to a pathology laboratory separate from the point of clinical care, the patient's personal records device card is sent by the examining physician with the samples to the laboratory. The latest data file is added to the personal records device card by the examining laboratory (or the point of care laboratory) and returned to the patient.

As is clear, each patient will possess the data that impacts on his or her own diseases and can present this data anywhere in the world. This aspect of the present invention eliminates the need to send for old pathological slides with the attendant loss of time and added expense in the course of the diagnostic process that leads to decisions about treatment. Moreover, given the variability in inter- and intra-observer interpretation of a given slide of tissue, the digitized data base (the vibrational spectrum of the patient's tissues) together with a uniform method for comparing spectra with each other, provide a basis for determining the progression or regression of disease in cells that is currently unavailable by any other means.

A benefit provided by the present invention is that all prior data files can be reexamined simply when new or revised methods are provided for analyzing a vibrational spectrum. For this purpose, the patient's data records contain, in addition to the spectral data, the dates of examination, codes that indicate the tissue examined, and the latest method used to analyze the spectra. The patient's personal records device card also contains identifiers for patient demographics, insurance, and any other pertinent information.

When a patient's personal records card indicates prior examinations and is presented at a point of care diagnostic site or is sent with samples to an off-site pathology laboratory, or other off-site diagnostic facility, the stored records are cross-referenced to the newly acquired data so that the current sample and the prior spectral data are down-loaded to the computer on-line with the spectrometer. The cross-referencing between a new sample and old data files permits the computer to analyze new data and compare it with old files. This signal may be sent to the computer by a bar code reader in the spectrometer that reads the appropriate, already cross-referenced bar code affixed to the sample holder (with the relevant patient's sample) just prior to the onset of data collection. All analyses of old data in relation to the newest examination are conducted automatically and on-line. A printout of the latest results in the context of older examinations is provided automatically by the system of the present invention. The storage of files on a personal records device card insures that all spectra are analyzed and compared according to the same method.

Examination of Cells and Tissues Using Infrared Spectroscopy

Vibrational spectroscopy can be carried out on tissues and cells with a minimum of preparation of the tissues or cells. In fact, cells and tissues can be examined in their natural state, that is with no preparation of the cells prior to placing them in the light-beam for infrared spectroscopic examination. Fixation also may be used which includes chemical fixation of tissues and cells. The choice of the method depends on the clinician's particular needs and requirements.

The absence of a need to prepare samples with the expertise of highly trained personnel or via complex instruments means that the method of vibrational spectroscopy, in addition to collecting an objective set of data about the characteristics of molecules in tissues and cells, can be applied rapidly and in the clinical setting or at any point of care.

Fixing cells and tissues by any means changes the spectral properties of tissues and cells. Although the effects of fixation on the vibrational spectra of the components of cells and tissues must be taken into account, such fixation imposes no inherent limitations on the vibrational method for collecting objective data for determining whether tissues or cells are normal or are diseased because the effects of fixation are controlled by comparing unknown samples with known samples of normal and diseased tissues and cells that were treated exactly as the unknown samples.

Because of problems in controlling the spontaneous rate of deterioration of molecules in untreated tissues or cells in their natural states, the preferred embodiment of the invention described here is to examine fixed samples of tissues when there is any chance of delay between obtaining the tissues and collecting the vibrational spectrum of the tissue. These delays could occur during point of care examinations or during transport of samples from sites of collection to sites of analysis. Therefore, in the preferred embodiment of the invention, tissues and cells are fixed at the site of collection.

When tissues, not cells, are used as samples, the material for examination may be taken from a larger piece of tissue by scraping with a sharp blade or it may be prepared by microtome sectioning of frozen tissues. The latter method requires specialized equipment that usually is not at the point of care.

Adequacy Of Cells

The number of cells examined has an impact on the reliability of a normal diagnosis. The data base file, e.g., the data representation of the spectrum, contain absolute values for absorption of infrared light at all the frequencies sampled. The absolute value of absorption at any frequency will be correlated through standardized spectra in a data base with the number of cells examined. From this correlation the number of cells examined will be determined for each unknown spectrum.

According to the present invention, all diagnoses will contain a statement as to the number of cells on which diagnosis is based. Because of differences in the chemical and physical structures of molecules in normal and diseased cells, the standards used for measuring and quantitating the number of cells examined will be coupled to the determination of normal cells or cells with disease. The parameters on which the system of the present invention makes decisions depend on the construction of suitable data bases of information and that these data bases will be different for different types of tissues.

Control Of The Sample And Analysis

Other than the number of cells examined, a sample could be contaminated with excess fixative or water, or with dirt that obscure features of the spectrum important for making a diagnosis. Samples that are inadequate for these sorts of reasons will be reported as inadequate for rendering a diagnosis because of artifacts secondary to preparing the samples. Once it is determined that a sample is free from artifacts induced by preparation, the task for analysis is classification of the type of disease.

The system of the present invention performs an analysis of samples of tissues and cells in about 90 seconds. This time includes data collection in which there is co-adding of interferograms collected from the tissue by Fourier-transform vibrational spectroscopy and data analysis, which takes only a few seconds.

Infrared spectra of human and animal tissues can be obtained by placing tissue (removed from a patient or an animal) on a crystal designed for attenuated total reflectance spectroscopy. The technology of attenuated total reflectance spectroscopy just referred can be used to collect vibrational spectra from tissues in a patient by inserting the crystal, through which infrared light is passed, into organs of the body and impinging the crystal on the surface of the organ. What is collected is the infrared spectra of the top layer of cells in contact with the surface of reflective crystal of the probe. Infrared spectra also can be collected from tissues in the living patients through the use of probes for reflectance spectroscopy.

The preferred method for examining tissues directly in patients, without removing portions of tissue or cells, is via attenuated total reflectance infrared spectroscopy. This may be accomplished by inserting a suitable probe into a region of the body of a living patient during surgery to identify, in intact organs, the borders of cancerous tissues and normal tissues. Relevant clinical data can be collected in the same way during laparoscopic surgery, during endoscopy of the lower or upper intestinal tract, and during probing of the uterine cavity, cystoscopy, bronchoscopy, colposcopy, arthroscopy, hysteroscopy, or image-guided insertion (CT scan or sohographic imaging) into a lesion embedded in a solid organ, such as the liver, the breast, a lymph node, or any lesion that can be identified by palpation or imaging. The technique also can be used to collect data on the presence of disease in a patient without removing tissue, and as a basis for determining what portions of tissue should be biopsied for routine pathological examination.

The vibrational spectra of the molecular components in cells can be obtained by infrared spectroscopy, either in the mid-infrared region or the near infrared region of light frequencies. Alternatively, the vibrational spectra of cells can be obtained by Raman spectroscopy, using as the incident beam light in the visible, the ultraviolet, or the infrared regions of frequencies. The technique of resonance Raman spectroscopy also can be used for collecting the vibrational spectra of selected types of molecules in cells by proper selection of the wavelength of the incident beam of light.

Only a few interferograms will be collected at each site according to the preferred embodiment of the present invention. As well, there will be a continuous display on a CRT to guide the clinician for real-time diagnosis of the tissue: is the tissue. To provide this information in real-time, the relevant spectrum for normal tissue (relevant to the tissue being examined) will be subtracted from the spectrum for the region of tissue sampled. In the case that the tissue sampled is normal, the resulting difference spectrum will be a flat line. The physician can then move the probe to another region of the tissue. In the case of disease, a difference spectrum different from a straight line will appear almost instantly on the screen, indicating the presence of disease. The area can then be probed over a longer period of time to collect spectra with a high signal-to-noise ratio, which maximizes the power of analysis of the spectrum. Spectra from diseased areas will be stored and analyzed continuously as new regions of an organ are sampled by the probe.

Relevant spectra acquired in the above manner will be stored as archival material by the examining facility and on personal records device cards. These will be given to the patient to be used later for comparison with samples probed at later dates of examination of these are required.

Clinical Research World Wide

The present invention will allow easy study of the medical significance of indeterminate samples (spectra) and for essentially instantaneous, world-wide collection of such spectra, which can then be used as a basis for correlating a patient's clinical state regardless of the disease. In this way, the clinical relevance of the parameters that constitute the data base can be continually upgraded.

For example, all indeterminate spectra can be forwarded on-line by modem to a central research facility for the diagnostic system that may be accessed by a pathologists. The data base file of the indeterminate spectrum carries this identifying code and can be analyzed to determine whether it corresponds to spectra collected elsewhere, which also were indeterminate. Correlation of clinical and pathological data, including the natural history of disease in patients with indeterminate spectra may lead to inserting new limits for certain diagnoses and/or the recognition of new diagnostic entities that have clinical significance. Therefore, the present invention is a powerful tool for conducting clinical research world-wide and for rapidly assembling into a single data base the world-wide experience in examination of human tissues and cells.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

I claim:

1. A method for detecting and diagnosing disease in cells, comprising the steps of:
   obtaining and storing in storage means first spectra in a predetermined frequency range for at least one cell that has been determined to be free of dysplasia;
   collecting and distributing cells in a predetermined manner on a predetermined surface with cell collecting means;
   generating second spectra with for at least one cell disposed on the predetermined surface with a spectrometer means;
   comparing the first and second spectra for variations in frequency bands for indicating dysplasia;
   diagnosing a level of dysplasia based on a number and magnitude of variations of the first and second spectra.

2. The method as recited in claim 1, wherein the collecting and distributing step includes collecting and distributing cells on a window of a sample holder.

3. The method as recited in claim 2, wherein the window and sample holder are transparent to infrared and Raman energies.

4. The method as recited in claim 1, wherein the generating step includes generating spectra based on vibrational spectroscopy.

5. The method as recited in claim 4, wherein the spectroscopy includes infrared spectroscopy.

6. A method for of detecting and diagnosing disease in epithelial cells, comprising the steps of:
   (a) obtaining and storing in storage means first spectra in a mid-infrared frequency range for at least one cell from a patient being tested that has been determined to have a specific predetermined state;
   (b) collecting cells from the patient being tested;
   (c) generating second spectra in the mid-infrared frequency range from the cells collected at step (b);
   (d) comparing the first and second spectra for variations caused by a predetermined condition; and
   (e) diagnosing a change of levels of dysplasia based on the comparison at step (d) for determining a degree of progression or regression of dysplasia, or whether there has been no change in dysplasia.

7. The method as recited in claim 6, wherein the mid-infrared frequency range is between 600–4000 $cm^{-1}$.

8. The method as recited in claim 6, wherein the collecting at step (b) is carried out by scraping.

9. The method as recited in claim 6, wherein the collecting at step (b) is carried out by surgical biopsy.

10. The method as recited in claim 6, wherein the collecting at step (b) is carried out by fine needle aspiration.

11. The method as recited in claim 6, wherein the collecting at step (b) is carried out by a collection of stool.

12. The method as recited in claim 6, wherein the collecting at step (b) is carried out by a collection of urine.

13. The method as recited in claim 6, wherein obtaining first spectra in step (a) is carried out using infrared transmission techniques.

14. The method as recited in claim 6, wherein obtaining first spectra in step (a) is carried out using infrared reflectance techniques.

15. The method as recited in claim 6, wherein obtaining first spectra in step (a) is carried out using infrared attenuated total reflectance (ATR) techniques.

16. The method as recited in claim 6, wherein obtaining first spectra in step (a) is carried out using multi-variable perturbation infrared techniques.

17. The method as recited in claim 6, wherein generating second spectra in step (c) is carried out using infrared transmission techniques.

18. The method as recited in claim 6, wherein generating second spectra in step (c) is carried out using infrared reflectance techniques.

19. The method as recited in claim 6, wherein generating second spectra in step (c) is carried out using infrared attenuated total reflectance (ATR) techniques.

20. The method as recited in claim 6, wherein generating second spectra in step (c) is carried out using multi-variable perturbation infrared techniques.

21. The method as recited in claim 6, wherein the method is used for detecting and diagnosing disease in epithelial cells in humans.

22. The method as recited in claim 6, wherein the method is used for detecting and diagnosing disease in epithelial cells in non-humans.

23. The method as recited in claim 22, wherein the method is used for detecting and diagnosing disease in epithelial cells in animals.

24. The method as recited in claim 6, wherein the method is used for detecting and diagnosing disease in epithelial cells in-vitro.

25. The method as recited in claim 6, wherein the specific predetermined state in step (a) is dysplasia.

26. The method as recited in claim 6, wherein the specific predetermined state in step (a) is non-dysplasia.

27. The method as recited in claim 6, wherein the specific predetermined state in step (a) is precancer.

28. The method as recited in claim 6, wherein the specific predetermined state in step (a) is frank cancer.

29. The method as recited in claim 6, wherein the predetermined condition in step (d) is dysplasia.

30. The method as recited in claim 6, wherein the predetermined condition in step (d) is inflammation.

31. The method as recited in claim 6, wherein the obtaining the first Raman spectra includes collecting said first spectra in-situ.

32. The method as recited in claim 31, wherein collecting said first spectra in-situ includes collecting with a sensing probe.

33. A method for detecting and diagnosing disease in epithelial cells of humans, comprising the steps of:

(a) obtaining and storing in storage means first spectra in a near-infrared frequency range for at least one cell from a patient being tested that has been determined to have a specific predetermined state;

(b) collecting cells from the patient being tested;

(c) generating second spectra in the near-infrared frequency range from the cells collected at step (b);

(d) comparing the first and second spectra for variations caused by a predetermined condition: and (e) diagnosing a change of levels of dysplasia based on the comparison at step (d) for determining a degree of progression or regression of dysplasia, or whether there has been no change in dysplasia.

34. The method as recited in claim 33, wherein the near-infrared frequency range is between 4000–10,000 $cm^{-1}$.

35. The method as recited in claim 33, wherein the collecting at step (b) may be carried out by scraping.

36. The method as recited in claim 33, wherein the collecting at step (b) is carrier out by surgical biopsy.

37. The method as recited in claim 33, wherein the collecting at step (b) is carried out by fine needle aspiration.

38. The method as recited in claim 33, wherein the collecting at step (b) is carried out by a collection of stool.

39. The method as recited in claim 33, wherein the collecting at step (b) is carried out by a collection of urine.

40. The method as recited in claim 33, wherein obtaining first spectra in step (a) is carried out using infrared transmission techniques.

41. The method as recited in claim 33, wherein obtaining first spectra in step (a) is carried out using infrared reflectance techniques.

42. The method as recited in claim 33, wherein obtaining first spectra in step (a) is carried out using infrared attenuated total reflectance (ATR) techniques.

43. The method as recited in claim 33, wherein obtaining first spectra in step (a) is carried out using multi-variable perturbation infrared techniques.

44. The method as recited in claim 33, wherein generating second spectra in step (c) is carried out using infrared transmission techniques.

45. The method as recited in claim 33, wherein generating second spectra in step (c) is carried out using infrared reflectance techniques.

46. The method as recited in claim 33, wherein generating second spectra in step (c) is carried out using infrared attenuated total reflectance (ATR) techniques.

47. The method as recited in claim 33, wherein generating second spectra in step (c) is carried out using multi-variable perturbation infrared techniques.

48. The method as recited in claim 33, wherein the method is used for detecting and diagnosing disease in epithelial cells in-vitro.

49. The method as recited in claim 33, wherein the specific predetermined state in step (a) is dysplasia.

50. The method as recited in claim 33, wherein the specific predetermined state in step (a) is non-dysplasia.

51. The method as recited in claim 33, wherein the specific predetermined state in step (a) is precancer.

52. The method as recited in claim 33, wherein the specific predetermined state in step (a) is frank cancer.

53. The method as recited in claim 33, wherein the predetermined condition in step (d) is dysplasia.

54. The method as recited in claim 33, wherein the predetermined condition in step (d) is inflammation.

55. The method as recited in claim 33, wherein the obtaining the first Raman spectra includes collecting said first spectra in-situ.

56. The method as recited in claim 55, wherein collecting said first spectra in-situ includes collecting with a sensing probe.

57. A method for of detecting and diagnosing disease in epithelial cells, comprising the steps of:

(a) obtaining and storing in storage means first Raman spectra for at least one cell from a patient being tested that has been determined to have a specific predetermined state;

(b) collecting cells from the patient being tested;

(c) generating second Raman spectra from the cells collected at step (b);

(d) comparing the first and second Raman spectra for variations caused by a predetermined condition: and (e) diagnosing a change of levels of dysplasia based on the comparison at step (d) for determining a degree of progression or regression of dysplasia, or whether there has been no change in dysplasia.

58. The method as recited in claim 57, wherein the collecting at step (b) is carrier out by scraping.

59. The method as recited in claim 57, wherein the collecting at step (b) is carried out by surgical biopsy.

60. The method as recited in claim 57, wherein the collecting at step (b) is carried out by fine needle aspiration.

61. The method as recited in claim 57, wherein the collecting at step (b) is carried out by a collection of stool.

62. The method as recited in claim 57, wherein the collecting at step (b) is carried out by a collection of urine.

63. The method as recited in claim 57, wherein the method is used for detecting and diagnosing disease in epithelial cells in humans.

64. The method as recited in claim 57, wherein the method is used for detecting and diagnosing disease in epithelial cells in non-humans.

65. The method as recited in claim 64, wherein the method is used for detecting and diagnosing disease in epithelial cells in animals.

66. The method as recited in claim 57, wherein the method is used for detecting and diagnosing disease in epithelial cells in-vitro.

67. The method as recited in claim 57, wherein the specific predetermined state in step (a) is dysplasia.

68. The method as recited in claim 57, wherein the specific predetermined state in step (a) is non-dysplasia.

69. The method as recited in claim 57, wherein the specific predetermined state in step (a) is precancer.

70. The method as recited in claim 57, wherein the specific predetermined state in step (a) is frank cancer.

71. The method as recited in claim 57, wherein the predetermined condition in step (d) is dysplasia.

72. The method as recited in claim 57, wherein the predetermined condition in step (d) is inflammation.

73. The method as recited in claim 57, wherein the frequency range of the Raman spectra is from ultraviolet to near-infrared.

74. The method as recited in claim 57, wherein the obtaining the first Raman spectra includes collecting said first spectra in-situ.

75. The method as recited in claim 74, wherein collecting said first spectra in-situ includes collecting with a sensing probe.

76. A method for of detecting and diagnosing disease in epithelial cells, comprising the steps of:

(a) obtaining and storing in storage means first resonance Raman spectra for at least one cell from a patient being tested that has been determined to have a specific predetermined state;

(b) collecting cells from the patient being tested;

(c) generating second Raman spectra from the cells collected at step (b);

(d) comparing the first and second resonance Raman spectra for variations caused by a predetermined condition: and (e) diagnosing a change of levels of dysplasia based on the comparison at step (d) for determining a degree of progression or regression of dysplasia, or whether there has been no change in dysplasia.

77. The method as recited in claim 76, wherein the collecting at step (b) is carried out by scraping.

78. The method as recited in claim 76, wherein the collecting at step (b) is carried out by surgical biopsy.

79. The method as recited in claim 76, wherein the collecting at step (b) is carried out by fine needle aspiration.

80. The method as recited in claim 76, wherein the collecting at step (b) is carried out by a collection of stool.

81. The method as recited in claim 76, wherein the collecting at step (b) is carried out by a collection of urine.

82. The method as recited in claim 76, wherein the method is used for detecting and diagnosing disease in epithelial cells in humans.

83. The method as recited in claim 76, wherein the method is used for detecting and diagnosing disease in epithelial cells in non-humans.

84. The method as recited in claim 83, wherein the method is used for detecting and diagnosing disease in epithelial cells in animals.

85. The method as recited in claim 76, wherein the method is used for detecting and diagnosing disease in epithelial cells in-vitro.

86. The method as recited in claim 76, wherein the specific predetermined state in step (a) is dysplasia.

87. The method as recited in claim 76, wherein the specific predetermined state in step (a) is non-dysplasia.

88. The method as recited in claim 76, wherein the specific predetermined state in step (a) is precancer.

89. The method as recited in claim 76, wherein the specific predetermined state in step (a) is frank cancer.

90. The method as recited in claim 76 wherein the predetermined condition in step (d) is dysplasia.

91. The method as recited in claim 76, wherein the predetermined condition in step (d) is inflammation.

92. The method as recited in claim 76, wherein the frequency range of the Raman spectra is from ultraviolet to near-infrared.

93. The method as recited in claim 76, wherein the obtaining the first Raman spectra includes collecting said first spectra in-situ.

94. The method as recited in claim 93, wherein collecting said first spectra in-situ includes collecting with a sensing probe.

95. A method for detecting and diagnosing disease in epithelial cells for grading on a continuous scale of a predetermined range from non-dysplastic to fully dysplastic, comprising the steps of:

(a) setting a first quantitative value along the continuous scale representative of a predetermined dysplastic condition for at least one cell of a patient being tested so that relative changes in a degree of dysplasia may be determined for said patient:

(b) collecting cells from the patient being tested;

(c) generating spectral information from the cells collected at step (b);

(d) determining a second quantitative value along the continuous scale that is representative of spectral information generated at step (c);

(e) comparing the first and second quantitative values on the continuous scale; and (f) determining based on the first and second quantitative values a degree of progression or regression of dysplasia, or whether there has been no change in dysplasia.

96. The method as recited in claim 95, wherein the method is used for detecting and diagnosing disease in epithelial cells in humans.

97. The method as recited in claim 95, wherein the method is used for detecting and diagnosing disease in epithelial cells in non-humans.

98. The method as recited in claim 97, wherein the method is used for detecting and diagnosing disease in epithelial cells in animals.

99. The method as recited in claim 98, wherein the method is used for detecting and diagnosing disease in epithelial cells in-vitro.

100. The method as recited in claim 95, wherein the collecting at step (b) is carried out by scraping.

101. The method as recited in claim 95, wherein the collecting at step (b) is carried out by surgical biopsy.

102. The method as recited in claim 95, wherein the collecting at step (b) is carried out by fine needle aspiration.

103. The method as recited in claim 98, wherein the collecting at step (b) is carried out by a collection of stool.

104. The method as recited in claim 98, wherein the collecting at step (b) is carried out by a collection of urine.

105. A method for detecting and diagnosing disease in epithelial cells for grading on a continuous scale of a predetermined range from non-dysplastic to fully dysplastic, comprising the steps of:

(a) setting a first quantitative value along the continuous scale representative of a predetermined dysplastic condition for at least one cell in a cell culture being tested so that relative changes in a degree of dysplasia may be determined for said cell culture;

(b) collecting cells from the cell culture being tested;

(c) generating spectral information from the cell collected at step (b);

(d) determining a second quantitative value along the continuous scale that is representative of spectral information generated at step (c);

(e) comparing the first and second quantitative values on the continuous scale; and (f) determining based on the first and second quantitative values a degree of progression or regression of dysplasia, or whether there has been no change in dysplasia.

106. The method as recited in claim 105, wherein the method is used for detecting and diagnosing disease in epithelial cells from humans.

107. The method as recited in claim 105, wherein the method is used for detecting and diagnosing disease in epithelial cells from non-humans.

108. The method as recited in claim 105, wherein the method is used for detecting and diagnosing disease in epithelial cells from animals.

109. The method as recited in claim 105, wherein the method is used for detecting and diagnosing disease in epithelial cells in-vitro.

110. The method as recited in claim 105, wherein the collecting at step (b) is carried out by scraping.

111. The method as recited in claim 105, wherein the collecting at step (b) is carried out by surgical biopsy.

112. The method as recited in claim 105, wherein the collecting at step (b) is carried out by fine needle aspiration.

113. The method as recited in claim 105, wherein the collecting at step (b) is carried out by a collection of stool.

114. The method as recited in claim 105, wherein the collecting at step (b) is carried out by a collection of urine.

115. A method for detecting and diagnosing disease in cells, comprising the steps of:
(a) obtaining first spectra in a predetermined frequency range for at least a first cell from a source;
(b) comparing the first spectra with a set of spectral data indicative of a plurality of states of dysplasia and determining a state of dysplasia for the first cell;
(c) collecting at least a second cell from the source;
(d) generating second spectra in a predetermined frequency range for the second cell;
(e) comparing the second spectra with the set of spectral data indicative of a plurality of states of dysplasia and determining a state of dysplasia for the second cell;
(f) comparing the state of dysplasia for the first cell and the state of dysplasia for the second cell; and
(g) diagnosing a change of levels of dysplasia based on the comparison at step (f) for determining a degree of progression or regression of dysplasia, or whether there have been no change in dysplasia.

116. The method as recited in claim 115, wherein the collecting step at step (c) is carried out by scraping.

117. The method as recited in claim 115, wherein the collecting step at step (c) is carried out by surgical biopsy.

118. The method as recited in claim 115, wherein the collecting step at step (c) is carried out by fine needle aspiration.

119. The method as recited in claim 115, wherein the collecting step at step (c) is carried out by a collection of stool.

120. The method as recited in claim 115, wherein the collecting step at step (c) is carried out by a collection of urine.

121. The method as recited in claim 115, wherein the method is used for detecting and diagnosing disease in humans.

122. The method as recited in claim 115, wherein the method is used for detecting and diagnosing disease in non-humans.

123. The method as recited in claim 115, wherein the method is used for detecting and diagnosing disease in animals.

124. The method as recited in claim 115, wherein obtaining first spectra in step (a) is carried out using infrared transmission techniques.

125. The method as recited in claim 115, wherein generating second spectra in step (d) is carried out using infrared transmission techniques.

126. A method for detecting and diagnosing disease in cells, comprising the steps of:
(a) obtaining and storing in storage means first spectra in at least one predetermined frequency range for at least a first cell from a source with the stored spectra being determined to have a specific state of dysplasia;
(b) collecting at least a second cell from the source;
(c) generating second spectra in at least one predetermined frequency range for the second cell collected at step (b);
(d) comparing the second spectra with a set of spectral data indicative of a plurality of states of dysplasia and determining a state of dysplasia for the second cell;
(e) comparing the state of dysplasia for the first cell with the state of dysplasia for the second cell; and
(f) diagnosing a change of levels of dysplasia based on the comparison at step (e) for determining a degree of progression or regression of dysplasia, or whether there has been no change in dysplasia.

127. The method as recited in claim 126, wherein the collecting step at step (b) is carried out by scraping.

128. The method as recited in claim 126, wherein the collecting step at step (b) is carried out by surgical biopsy.

129. The method as recited in claim 126, wherein the collecting step at step (b) is carried out by fine needle aspiration.

130. The method as recited in claim 126, wherein the collecting step at step (b) is carried out by a collection of stool.

131. The method as recited in claim 126, wherein the collecting step at step (b) is carried out by a collection of urine.

132. The method as recited in claim 126, wherein the method is used for detecting and diagnosing disease in humans.

133. The method as recited in claim 126, wherein the method is used for detecting and diagnosing disease in non-humans.

134. The method as recited in claim 126, wherein the method is used for detecting and diagnosing disease in animals.

135. The method as recited in claim 126, Wherein obtaining first spectra in step (a) is carried out using infrared transmission techniques.

136. The method as recited in claim 126, wherein generating second spectra in step (c) is carried out using infrared transmission techniques.

137. A method for detecting and diagnosing disease in cells, comprising the steps of:
(a) obtaining and storing in storage means first spectra in a near-infrared frequency range for at least a first cell from a source with the stored spectra being determined to have a specific state of dysplasia;
(b) collecting at least a second cell from the source;
(c) generating second spectra in a near-infrared frequency range for the second cell collected at step (b);
(d) comparing the second spectra with a set of spectral data indicative of a plurality of states of dysplasia and determining a state of dysplasia for the second cell;
(e) comparing the state of dysplasia for the first cell with the state of dysplasia for the second cell; and
(f) diagnosing a change of levels of dysplasia based on the comparison at step (e) for determining a degree of progression or regression of dysplasia, or whether there has been no change in dysplasia.

138. The method as recited in claim 137, wherein the collecting step at step (b) is carried out by scraping.

139. The method as recited in claim 137, wherein the collecting step at step (b) is carried out by surgical biopsy.

140. The method as recited in claim 137, wherein the collecting step at step (b) is carried out by fine needle aspiration.

141. The method as recited in claim 137, wherein the collecting step at step (b) is carried out by a collection of stool.

142. The method as recited in claim 137, wherein the collecting step at step (b) is carried out by a collection of urine.

143. The method as recited in claim 137, wherein the method is used for detecting and diagnosing disease in humans.

144. The method as recited in claim 137, wherein the method is used for detecting and diagnosing disease in non-humans.

145. The method as recited in claim 137, wherein the method is used for detecting and diagnosing disease in animals.

146. The method as recited in claim 137, wherein obtaining first spectra in step (a) is carried out using infrared transmission techniques.

147. The method as recited in claim 137, wherein generating second spectra in step (c) is carried out using infrared transmission techniques.

148. A method for detecting and diagnosing disease in cells, comprising the steps of:
 (a) obtaining and storing in storage means first Raman spectra for at least a first cell from a source with the stored spectra being determined to have a specific state of dysplasia;
 (b) collecting at least a second cell from the source;
 (c) generating second Raman spectra for the second cell collected at step (b);
 (d) comparing the second spectra with a set of spectral data indicative of a plurality of states of dysplasia and determining a state of dysplasia for the second cell;
 (e) comparing the state of dysplasia for the first cell with the state of dysplasia for the second cell; and
 (f) diagnosing a change of levels of dysplasia based on the comparison at step (e) for determining a degree of progression or regression of dysplasia, or whether there has been no change in dysplasia.

149. The method as recited in claim 148, wherein the collecting step at step (b) is carried out by scraping.

150. The method as recited in claim 148, wherein the collecting step at step (b) is carried out by surgical biopsy.

151. The method as recited in claim 148, wherein the collecting step at step (b) is carried out by fine needle aspiration.

152. The method as recited in claim 148, wherein the collecting step at step (b) is carried out by a collection of stool.

153. The method as recited in claim 148, wherein the collecting step at step (b) is carried out by a collection of urine.

154. The method as recited in claim 148, wherein the method is used for detecting and diagnosing disease in humans.

155. The method as recited in claim 148, wherein the method is used for detecting and diagnosing disease in non-humans.

156. The method as recited in claim 148, wherein the method is used for detecting and diagnosing disease in animals.

157. The method as recited in claim 148, wherein obtaining first spectra in step (a) is carried out using Raman techniques.

158. The method as recited in claim 148, wherein generating second spectra in step (c) is carried out using Raman techniques.

159. A method for detecting and diagnosing disease in cells, comprising the steps of:
 (a) obtaining and storing in storage means first resonance Raman spectra for at least a first cell from a source with the stored spectra being determined to have a specific state of dysplasia;
 (b) collecting at least a second cell from the source;
 (c) generating second resonance Raman spectra for the second cell collected at step (b);
 (d) comparing the second spectra with a set of spectra data indicative of a plurality of states of dysplasia and determining a state of dysplasia for the second cell;
 (e) comparing the state of dysplasia for the first cell with the state of dysplasia for the second cell; and
 (f) diagnosing a change of levels of dysplasia based on the comparison at step (e) for determining a degree of progression or regression of dysplasia, or whether there has been no change in dysplasia.

160. The method as recited in claim 159, wherein the collecting step at step (b) is carried out by scraping.

161. The method as recited in claim 159, wherein the collecting step at step (b) is carried out by surgical biopsy.

162. The method as recited in claim 159, wherein the collecting step at step (b) is carried out by fine needle aspiration.

163. The method as recited in claim 159, wherein the collecting step at step (b) is carried out by a collection of stool.

164. The method as recited in claim 159, wherein the collecting step at step (b) is carried out by a collection of urine.

165. The method as recited in claim 159, wherein the method is used for detecting and diagnosing disease in humans.

166. The method as recited in claim 159, wherein the method is used for detecting and diagnosing disease in non-humans.

167. The method as recited in claim 159, wherein the method is used for detecting and diagnosing disease in animals.

168. The method as recited in claim 159, wherein obtaining first spectra in step (a) is carried out using resonance Raman techniques.

169. The method as recited in claim 159, wherein generating second spectra in step (c) is carried out using resonance Raman techniques.

170. A method for detecting and diagnosing disease in cells for grading on a continuous scale of a predetermined range from non-dysplastic to fully dysplastic, comprising the steps of:
 (a) setting a first quantitative value along the continuous scale representative of a predetermined dysplastic condition for at least one cell of a source so that relative changes in a degree of dysplasia may be determined for the source;
 (b) collecting cells from the source;
 (c) generating spectral information from the cells collected at step (b);
 (d) determining a second quantitative value along the continuous scale that is representative of spectral information generated at step (c);
 (e) comparing the first and second quantitative values on the continuous scale; and
 (f) determining based on the first and second quantitative values a degree of progression or regression of dysplasia, or whether there has been no change in dysplasia.

171. The method as recited in claim 170, wherein the collecting step at step (b) is carried out by scraping.

172. The method as recited in claim 170, wherein the collecting step at step (b) is carried out by surgical biopsy.

173. The method as recited in claim 170, wherein the collecting step at step (b) is carried out by fine needle aspiration.

174. The method as recited in claim 170, wherein the collecting step at step (b) is carried out by a collection of stool.

175. The method as recited in claim 170, wherein the collecting step at step (b) is carried out by a collection of urine.

176. The method as recited in claim 170, wherein the method is used for detecting and diagnosing disease in humans.

177. The method as recited in claim 170, wherein the method is used for detecting and diagnosing disease in non-humans.

178. The method as recited in claim 170, wherein the method is used for detecting and diagnosing disease in animals.

179. The method as recited in claim 170, generating spectral information in step (c) is carried out using infrared transmission techniques.

180. A method for detecting and diagnosing disease in cells for grading on a continuous scale of a predetermined range from non-dysplastic to fully dysplastic, comprising the steps of:

(a) setting a first quantitative value along the continuous scale representative of a predetermined dysplastic condition for at least one cell in a cell culture so that relative changes in a degree of dysplasia may be determined for the source;

(b) collecting cells from the source;

(c) generating spectral information from the cells collected at step (b);

(d) determining a second quantitative value along the continuous scale that is representative of spectral information generated at step (c);

(e) comparing the first and second quantitative values on the continuous scale; and (f) determining based on the first and second quantitative values a degree of progression or regression of dysplasia, or whether there has been no change in dysplasia.

181. The method as recited in claim 180, wherein the collecting step at step (b) is carried out by scraping.

182. The method as recited in claim 180, wherein the collecting step at step (b) is carried out by surgical biopsy.

183. The method as recited in claim 180, wherein the collecting step at step (b) is carried out by fine needle aspiration.

184. The method as recited in claim 180, wherein the collecting step at step (b) is carried out by a collection of stool.

185. The method as recited in claim 180, wherein the collecting step at step (b) is carried out by a collection of urine.

186. The method as recited in claim 180, wherein the method is used for detecting and diagnosing disease in humans.

187. The method as recited in claim 180, wherein the method is used for detecting and diagnosing disease in non-humans.

188. The method as recited in claim 180, wherein the method is used for detecting and diagnosing disease in animals.

189. The method as recited in claim 180, generating spectral information in step (c) is carried out using infrared transmission techniques.

* * * * *